US012129346B2

(12) United States Patent
Sels et al.

(10) Patent No.: US 12,129,346 B2
(45) Date of Patent: Oct. 29, 2024

(54) FRACTIONATION AND DEPOLYMERISATION OF LIGNOCELLULOSIC MATERIAL

(71) Applicant: KATHOLIEKE UNIVERSITEIT LEUVEN, Leuven (BE)

(72) Inventors: Bert Sels, Westerlo (BE); Tom Renders, Leuven (BE); Elias Cooreman, Bouwel (BE); Sander Van Den Bosch, Boortmeerbeek (BE)

( * ) Notice: Subject to any disclaimer, the term of this patent is extended or adjusted under 35 U.S.C. 154(b) by 606 days.

(21) Appl. No.: 17/255,163

(22) PCT Filed: Jun. 25, 2019

(86) PCT No.: PCT/EP2019/066887
§ 371 (c)(1),
(2) Date: Dec. 22, 2020

(87) PCT Pub. No.: WO2020/002361
PCT Pub. Date: Jan. 2, 2020

(65) Prior Publication Data
US 2021/0269616 A1    Sep. 2, 2021

Related U.S. Application Data

(60) Provisional application No. 62/689,655, filed on Jun. 25, 2018.

(51) Int. Cl.
C08J 11/16    (2006.01)
B01J 19/00    (2006.01)
C07C 27/06    (2006.01)
(52) U.S. Cl.
CPC .......... C08J 11/16 (2013.01); B01J 19/0013 (2013.01); C07C 27/06 (2013.01);
(Continued)

(58) Field of Classification Search
CPC .... C08J 11/16; C08J 2397/02; B01J 19/0013; B01J 2219/00051; B01J 2219/00162; C07C 27/06
(Continued)

(56) References Cited

U.S. PATENT DOCUMENTS 9,783,474 B2    10/2017  Delgass et al.
2009/0176286 A1   7/2009  O'Connor et al.
(Continued)

FOREIGN PATENT DOCUMENTS

EP    2891748 A1    7/2015
FR    3030561       12/2018
(Continued)

OTHER PUBLICATIONS

Cabiac et al., FR 3030561 A1 machine translation in English, Jun. 24, 2016. (Year: 2016).*
(Continued)

Primary Examiner — David T Karst
(74) Attorney, Agent, or Firm — Dinsmore & Shohl LLP

(57) ABSTRACT

Biomass is processed in a close to equivolumetric mixture of an alcohol and water at elevated temperature, in the presence of a metal catalyst and hydrogen. During this one-pot fractionation process, the hot liquor disentangles the polymeric biomass and depolymerises lignin and hemicellulose, while the catalyst and reductive environment are essential to accumulate and target stable products at high yield (such as phenolics and polyols, respectively). The process is particularly industrially relevant because its overcomes difficult and complex separation protocols, at place in classic biorefinery technology; the process foresees simple product recuperation in one process step into the three fractions; the solid carbohydrate pulp (mainly cellulose) is retrieved upon filtration, while phase separation of n-butanol and water occurs (Continued)

below 125° C. The three resulting product streams provide a versatile platform for down-stream conversion towards added-value bio-based chemicals.

13 Claims, 18 Drawing Sheets

(52) U.S. Cl.
CPC .............. *B01J 2219/00051* (2013.01); *B01J 2219/00162* (2013.01); *C08J 2397/02* (2013.01)

(58) Field of Classification Search
USPC ........................................................ 530/507
See application file for complete search history.

(56) References Cited

U.S. PATENT DOCUMENTS

| | | | |
|---|---|---|---|
| 2016/0024712 | A1 | 1/2016 | Smit et al. |
| 2017/0152278 | A1 | 6/2017 | Samec et al. |

FOREIGN PATENT DOCUMENTS

| | | |
|---|---|---|
| WO | 2010/026244 A1 | 3/2010 |
| WO | 2015/158633 A1 | 10/2015 |
| WO | 2017178513 A1 | 10/2017 |

OTHER PUBLICATIONS

Yan, et al., "Selective Degradation of Wood Lignin over Noble-Metal Catalysts in a Two-Step Process", ChemSusChem, vol. 1, pp. 626-629, 2008.
Li, et al., "One-pot catalytic hydrocracking of raw woody biomass into chemicals over supported carbide catalysts: simultaneous conversion of cellulose hemicellulose and lignin", Energy & Environmental Science, pp. 1-8, 2011.
Van Den Bosch, et al., "Reductive lignocellulose fractionation into soluble lignin-derived phenolic monomers and dimers and processable carbohydrate pulps", Energy and Environmental Science, vol. 8, pp. 1748-1763, 2015.
Van Den Bosch, et al., "Tuning the lignin oil OH-content with Ru and Pd catalyst during lignin hydrogenolysis on birch wood", CemComm, pp. 1-4, 2015.
Anderson, et al., "Reductive Catalytic Fractionation of Corn Stover Lignin", ACS Sustainable Chemistry & Engineering, pp. A-K, 2016.
Shuai, et al., "Formaldehyde stabilization facilitates lignin monomer production during biomass deploymerization", Science, vol. 354, Issue 6310, pp. 329-334, Oct. 21, 2016.
Renders, et al., "Influence of Acidic ($H_3PO_4$) and Alkaline (NaOH) Additives on the Catalytic Reductive Fractionation of Lignocellulose", American Chemical Society, vol. 6, pp. 2055-2066, 2016.
Renders, et al., "Synergetic Effects of Alcohol/Water Mixing on the Catalytic Reductive Fractionation of Poplar Wood", ACS Sustainable Chemistry & Engineering, vol. 4, pp. 6894-6904, 2016.
Liu, et al., "Production of $C_5/C_6$ Sugar Alcohols by Hydrolytic Hydrogenation of Raw Lignocellulosic Biomass over Zr Based Solid Acids Combines with Ru/C", ACS Sustainable Chemistry & Engineering, vol. 5, pp. 5940-5950, 2017.
Van Den Bosch, et al., "Integrating lignin valorization and bio-ethanol production: on the role of Ni—$Al_2O_3$ catalysts pellets during lignin-frist fractionation", Green Chemistry, pp. 1-14, 2017.
Ferrini, et al., "Catalytic Biofining of Plant Biomass to Non-Pyrolytic Bio-Oil and Carbohydrates through Hydrogen Transfer Reactions", Angewandte communications, vol. 53, pp. 8634-8639, 2014.
Galkin, et al., "Hydrogen-free catalytic fractionation of woody biomass", ChemSusChem, vol. 9, pp. 3280-3287, 2016.
Galkin, et al., "Selective Route to 2-Propenyl Aryls Directly from Wood by a Tandem Organosolv and Palladium-Catalysed Transfer Hydrogenolysis", ChemSusChem, vol. 7, pp. 2154-2158, 2014.
Lan, et al., "Protection Group Effects During a,y-Diol Lignin Stabilization Promote High-Selectivity Monomer Production", Agnew Chem. Int. Ed., vol. 57, pp. 1356-1360, 2018.
Graça, et al., "Formation of Fate of Carboxylic Acids in the Lignin-First Biorefining of Lignocellulose via H-Transfer Catalyzed by Raney Ni", ACS Sustainable Chemistry & Engineering, vol. 6, pp. 13408-13419, 2018.
Vom Stein, et al., "From biomass to feedstock: one-step fractionation of lignocellulose components by the selective organic acid-catalyzed deploymerization of hemicellulose in a biphasic system", Green Chemistry, vol. 13, pp. 1772-1777, 2011.
Grande, et al., "Fractionation of lignocellulosic biomass using the OrganoCat process", Green Chemistry, vol. 17, pp. 3533-3539, 2015.
International Search Report pertaining to PCT Application No. PCT/EP2019/066887, filed Jun. 25, 2019, 4 pages.
Kumaniaev, et al., "Lignin depolymerization to monophenolic compounds in a flow-through system", Green Chemistry Communication, vol. 19, pp. 5767-5771, 2017.

\* cited by examiner

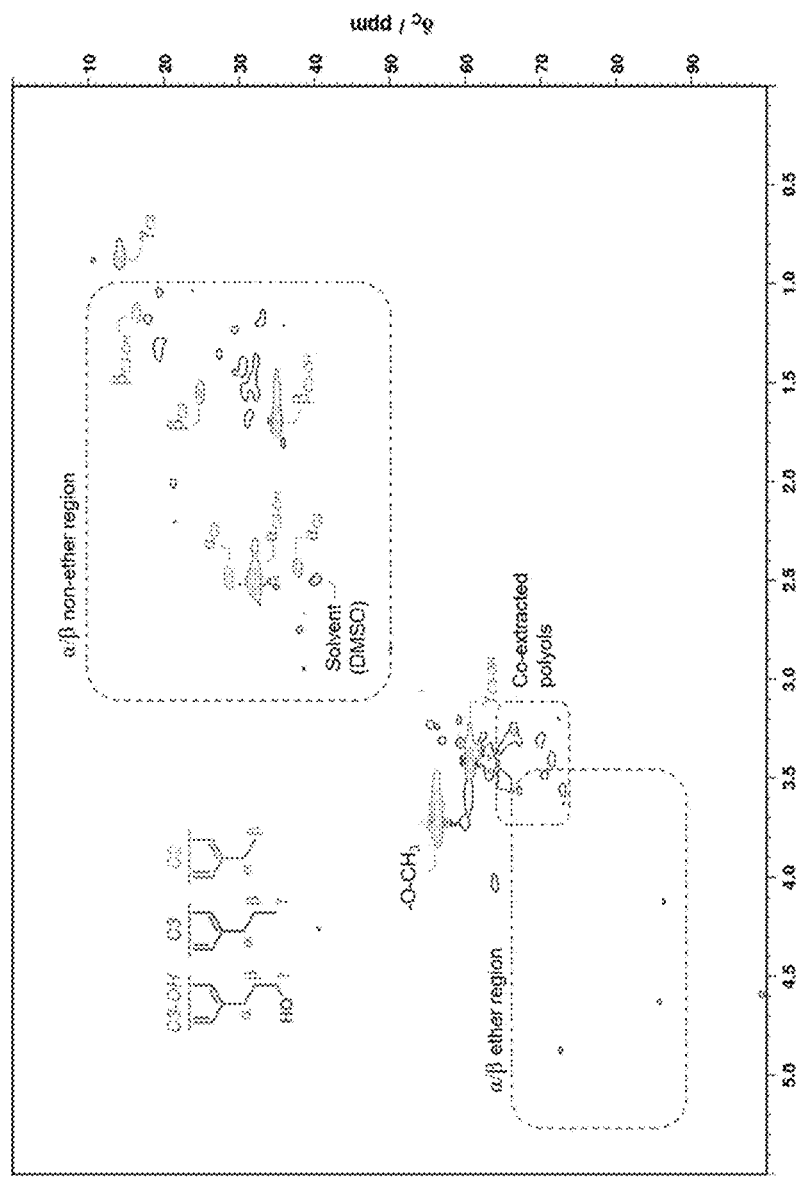
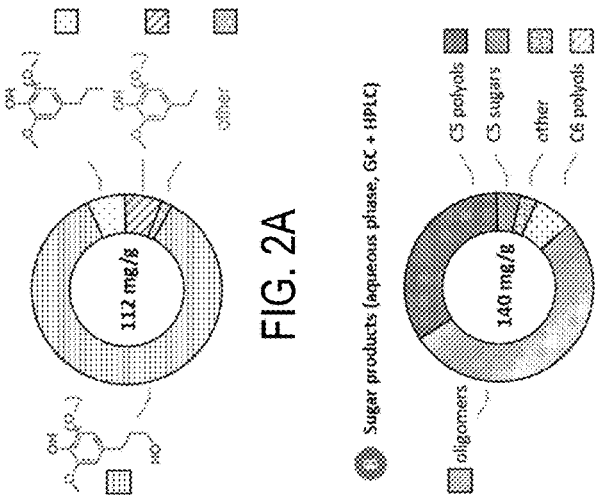
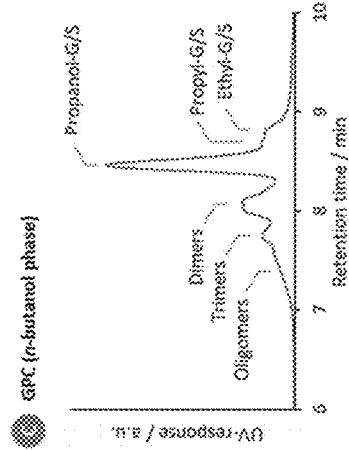
FIG. 2A
FIG. 2B
FIG. 2C
FIG. 2D

FRACTIONATION AND DEPOLYMERISATION OF LIGNOCELLULOSIC MATERIAL

CROSS-REFERENCES TO RELATED APPLICATIONS

This application is a national-stage application under 35 U.S.C. § 371 of International Application No. PCT/EP2019/066887, filed Jun. 25, 2019, which claims the benefit of priority to U.S. Provisional Application Ser. No. 62/689,655, filed Jun. 25, 2018.

FIELD OF THE INVENTION

In general the present invention concerns, catalytic lignocellulose biorefining using a mixture of an alcohol solvent and water—for instance n-butanol/water—toward phenolics, polyols, and cellulose. A process to convert lignocellulosic material into (i) lignin-derived phenolic compounds with propanol-sidechain, (ii) hemicellulose-derived polyols and oligosaccharides, and (iii) a cellulosic pulp by treating lignocellulosic material in presence of a transition metal catalyst under reducing atmosphere. The invention further relates to separation of the product streams obtainable by the process.

BACKGROUND

Lignocellulosic material is regarded as a promising resource for the bio-economy. Within this context, there is an increasing interest to use lignocellulosic material as a renewable feedstock for the production of chemicals, materials, fuels.

Lignocellulosic material includes, but is not limited to, wood, wood chips, bark, wood sawdust, timber, genetically engineered wood, waste wood, plant litter, herbaceous crops, straw, corn stover, sugar cane bagasse, rice husks, flax shives.

Lignocellulosic material is a composite material mainly consisting of three quantifiable biopolymers: cellulose, hemicellulose, and lignin. The cellulose portion is composed of linear chains of glucose units. The hemicellulose represents a family of branched carbohydrate polymers containing both pentoses and hexoses including xylose, arabinose, galactose, glucose and mannose. Lignin comprises an irregular polymer of aromatic and oxygenated units.

A common way to utilise lignocellulosic material is to fractionate the material in its major constituents. Degradation reactions often occur during fractionation, especially involving lignin and/or hemicellulose, resulting in low-value products. Degradation involves the formation of C—C bonds, which is often denoted as repolymerisation or condensation. Degraded products generally have a high molecular weight as a result of repolymerisation, and therefore are solid products. Examples are humins and so-called technical lignins. The formed C—C bonds are more difficult to cleave compared to the original ether bonds in the lignocellulose constituents.

Degradation reactions are caused by compounds that are unstable under the reaction conditions. Such unstable compounds typically bear a C=O or C=C functional group.

Examples of such unstable compounds include, but are not limited to, xylose, glucose, furfural, hydroxymethylfurfural, coniferyl alcohol, sinapyl alcohol, phenolic compounds with $C_2$-aldehyde substituents, and Hibbert's ketones. These unstable compounds can be transformed to stable compounds by transforming the C=O and/or C=C functional groups, for instance through hydrogenation.

An particular method for lignocellulose fractionation, performed by the pulp and paper industry, utilizes an aqueous mixture of NaOH and $Na_2S$ at 130-180° C. The major portion of the lignin and hemicellulose is readily dissolved in this process, and subsequently undergoes degradation reactions. The lignin and hemicellulose degradation products have low value to the industry, and are primarily incinerated for energy recuperation. The main valuable product of this process is a cellulose-enriched solid (the so called "pulp"), which is used for production of paper and cardboard.

Another particular method for lignocellulose fractionation uses a water-soluble organic solvent such as ethanol in combination with water and/or acid to extract lignin and hemicellulose from the lignocellulosic material at elevated temperature (120-280° C.), as disclosed in US20160024712A1 and US20090176286A1. The cellulose fraction is obtained in the form of a solid residue that can be used for commercial pulp applications. The main fraction of the hemicellulose is converted into sugars and/or degradation products, depending on the process severity. The lignin fraction undergoes degradation reactions. The solubilised lignin is separated from the solubilised hemicellulose-derived products through precipitation yielding an isolated solid product with high Mw (>1500 g·mol$^{-1}$). Due to the degraded nature of the lignin, it is difficult to convert the lignin into low Mw products, such as monomeric phenols.

Yet another method for fractionation of lignocellulosic material uses a mixture of water and an organic solvent that is at least partially immiscible with water at the reaction temperature (85-150° C.), in combination with a carboxylic acid catalyst, as disclosed in WO2012110231A1. Examples of water-immiscible solvents include 2-methyltetrahydrofuran and 3-methyltetrahydrofuran. The hemicellulose is extracted and depolymerised into sugars such as xylose, which are retained in the aqueous phase. The lignin is extracted and contained in the organic phase, and undergoes degradation reactions, resulting in a high Mw product. The lignin is obtained as a solid after solvent evaporation. The cellulose is retained in the solid residue which is recovered as a pulp upon filtration. Owing to the different partition of the solubilised products (sugars and lignin) in the biphasic solvent system, the solubilised products are easily separated (Grande, et al., Green Chemistry, 2015, 3533-3539; vom Stein, et al., Green Chemistry, 2011, 1772-1777), without the need for precipitation as performed in single phase systems (US20160024712A1).

Yet another method for fractionation of lignocellulosic material uses a mixture of water and an organic solvent, in combination with an aldehyde such as formaldehyde (WO2017178513A1) to stabilise solubilised products and prevent degradation. The lignin is obtained as a solid high Mw product with chemically bound aldehyde, and can be recovered from the liquor through precipitation. A second step is required to convert the lignin into low Mw products, such as monomeric phenols. Owing to the stabilisation with the aldehyde, the yield of obtained monophenolic products in the second step is close to the theoretical maximum—the absolute value varies between different plant types (Shuai, et al., Science, 2016, 329-333; Lan, et al., Angewandte Chemie International Edition, 2018, 1356-1360). During solvent-assisted lignocellulose fractionation in presence of aldehydes, the hemicellulose is converted into furfural and stabilised sugars. The structure of the latter depends on the structure of the aldehyde. In case of formaldehyde, formylated sugars such as diformyl xylose are obtained (WO2017178513A1). The cellulose fraction is obtained as a solid product which includes chemically bound aldehyde.

Another method to fractionate lignocellulosic material involves treating biomass in an organic solvent or in a mixture of water-miscible solvent and water, in presence of a transition metal catalyst. This method, herein referred to as "catalytic fractionation", combines lignocellulose fractionation with catalytic conversion of solubilised lignin towards compounds that are stable under the reaction conditions. Catalytic conversion of lignin thus omits the problem of degradation of lignin. The obtained lignin has a low molecular weight (<1500 g·mol$^{-1}$) and is a viscous liquid oil—comprises phenolic monomers, dimers, and oligomers—in contrast to a solid lignin. The yield of monophenolic products is close to the theoretical maximum—the absolute value varies between different plant types. The monomer yield is typically in the range of 20-60 wt % for hardwood species, and 10-30 wt % for softwood species.

EP2891748A1 discloses the catalytic fractionation of lignocellulosic material in a mixture of water and a secondary alcohol (such as isopropanol) at 170-240° C., in presence of a skeletal nickel catalyst and in absence of hydrogen. The alcohol serves as H-donor. In this method, the lignin is catalytically converted into a low Mw lignin oil, in addition to a pulp containing both the hemicellulose and cellulose in solid form (EP2891748A1; Ferrini and Rinaldi, Angewandte Chemie International Edition, 2014, 8634-8639). Part of the solvent in converted into the corresponding aldehyde/ketone, for example isopropanol is converted into acetone. The lignin oil is rich in a variety of compounds, including 4-(3-hydroxy-propyl)-guaiacol, 4-(3-hydroxy-propyl)-syringol, 4-n-propylguaiacol, 4-n-propylsyringol, and also cyclohexanols. Degradation of solubilised sugars occurs (Rinaldi et al. ACS Sustainable Chem. Eng. 2018, 6, 13408-13419). Solubilised hemicellulose sugars are not stabilised in this method.

US20170152278A1 discloses the catalytic fractionation of lignocellulosic material using a mixture of water and water-miscible alcohol such as methanol and ethanol, at 160-190° C. The method uses a Pd-based catalyst in absence of hydrogen to convert and stabilise the extracted lignin. In this method, the lignin is catalytically converted into a low Mw lignin oil, containing high amounts of phenolic molecules, mainly 4-(2-propenyl)guaiacol and 4-(2-propenyl) syringol (US20170152278A1, Galkin and Samec, ChemSusChem, 2014, 2154-2158). The cellulose is recovered in the form of a carbohydrate pulp. Part of the hemicellulose is retained as polymer in the pulp, depending on process severity. Part of the hemicellulose is solubilised and undergoes degradation (Galkin, et al., ChemSusChem, 2016, 3280-3287; Kumaniaev, et al., Green Chemistry, 2017, 5767-5771), thereby serving as H-donor for the process. After reaction, solvent purification is needed to remove sugar-derived degradation products from the lignin product oil, which involves the utilisation of additional solvents other than the reaction solvent.

Another catalytic fractionation method of lignocellulosic material uses a mixture of water and water-miscible alcohol such as methanol or ethanol, at 200° C., in combination with a Pd-based catalyst and pressurised hydrogen (20 bar) (Renders et al., ACS Sustainable Chem. Eng., 2016, 4, 6894-6904). In this method, the lignin is catalytically converted into a low Mw lignin oil, containing high amounts of phenolic molecules, mainly 4-(3-hydroxy-propyl)-guaiacol and 4-(3-hydroxy-propyl)-syringol. Part of the hemicellulose is solubilised and undergoes degradation. Solubilised hemicellulose sugars are not stabilised in this method.

U.S. Pat. No. 9,783,474B2 discloses the catalytic fractionation of lignocellulosic material in methanol at 225° C. in presence of a palladium-zinc catalyst under hydrogen atmosphere. In this method, the lignin is catalytically converted into a low Mw lignin oil comprising 4-n-propylguaiacol and 4-n-propylsyringol. The cellulose is recovered in the form of a carbohydrate pulp. Part of the hemicellulose is retained as polymer in the pulp, depending on process severity. Part of the hemicellulose is solubilised in the form of methylated sugars, such as methyl xyloside. After reaction, solvent evaporation followed by liquid-liquid extraction is needed to obtain a purified lignin oil and isolated methylated sugars. Liquid-liquid extraction can be performed with water:dichloromethane (Renders et al., ACS Catalysis, 2016, 2055-2066) or water:ethylacetate.

Van den Bosch et al. disclose the catalytic fractionation of lignocellulosic material in methanol at 250° C. in presence of a Ru/C catalyst under hydrogen atmosphere (Energy & Environmental Science, 2015, 1748-1763). In this method, the lignin is catalytically converted into a low Mw lignin oil (<1500 g·mol$^{-1}$), containing high amounts of phenolic monomers (50 wt % relative to the initial lignin), mainly 4-n-propylguaiacol and 4-n-propanolguaiacol. When using Pd/C instead of Ru/C, approximately equal amounts of monomers are obtained (49 wt %), but mainly 4-(3-hydroxy-propyl)-guaiacol and 4-(3-hydroxy-propyl)-syringol (Van den Bosch et al., Chemical Communications, 51, 13158).

It is generally known that Ru-based catalysts result in mainly propyl-substituted phenolic monomers (more than 50% of the monomers), whereas Pd-based catalysts result in mainly (3-hydroxy-propyl)-substituted monomers (so called "propanol-substituted monomers", more than 50% of the monomers) (Van den Bosch et al., Chemical Communications, 51, 13158; Anderson et al., ACS Sustainable Chem. Eng. 2016, 4, 6940-6950; Van den Bosch, et al., Energy & Environmental Science, 2015, 1748-1763; Renders et al., ACS Sustainable Chem. Eng., 2016, 4, 6894-6904; Shuai et al., Science, 2016, 354, 329-333).

Yan et al. disclose the catalytic fractionation of lignocellulosic material in pure water using different noble metal catalysts (ChemSusChem 2008, 1, 626-629). High yields of phenolic monomers are obtained when a Pt-, Rh-, or Pd-based catalyst is used (19.7-33.6% on mass basis relative to the lignin content of the lignocellulosic material). When using a Ru-based catalyst under the same reaction conditions, a low monomer yield of 4.6 wt % is obtained; exemplifying that Ru-based catalyst is not an effective catalyst for catalytic fractionation of lignocellulose in water.

Yet another catalytic fractionation process of lignocellulosic material is the so-called hydrolytic hydrogenation. Liu, et al., (ACS Sustainable Chemistry & Engineering, 2017, 5940-5950) disclose the hydrolytic hydrogenation of lignocellulosic material in pure water at 200° C. in presence of ZrP and Ru/C under pressurised hydrogen atmosphere. Both the cellulose and hemicellulose are solubilised and catalytically converted into polyols such as sorbitol and xylitol. The lignin undergoes degradation reactions, and is retrieved as a water-insoluble solid. The process thus results in two products streams.

Yet another approach is the so called "one-pot catalytic hydrocracking" of lignocellulosic material, disclosed by Li, et al., Energy & Environmental Science, 2012, 6383-6390. In this process, lignocellulosic material is treated in water at 245° C., in presence of a $W_2C$ catalyst under pressurised hydrogen. During this process, the entire biomass is solubilised in contrast to earlier discussed 'catalytic fractionation' wherein the cellulose is retrieved as a solid. In one-pot catalytic hydrocracking, both the cellulose and hemicellulose fraction are catalytically converted into polyols including ethylene glycol, 1,2-propylene glycol, and 1,2-butylene glycol. The lignin is catalytically converted into a low Mw product mixture, rich in monophenolic compounds such as 4-(3-hydroxy-propyl)-guaiacol, 4-(3-hydroxy-propyl)-syringol, 4-n-propylguaiacol, 4-n-propylsyringol. Additional product work up is required to separate the phenolic compounds from the polyols, for example through liquid-liquid extraction.

Therefore, there is an unmet need for a process to convert lignocellulosic material into (i) a lignin-derived product stream comprising monophenolic compounds, diphenolic compounds, and small oligomeric phenolic compounds; (ii) a hemicellulose-derived stream comprising polyols such as xylitol and mannitol, and oligosaccharides; and (iii) a cellulose-enriched solid material. In addition, easy product separation and controllable product selectivity are desirable features. More in particularly, a high selectivity towards 4-(3-hydroxy-propyl)-guaiacol and 4-(3-hydroxy-propyl)-syringol is desirable. A high selectivity towards 4-(3-hydroxy-propyl)-guaiacol and 4-(3-hydroxy-propyl)-syringol is defined here as higher than 60 wt % of the obtained monomer products, such as higher than 80 wt %.

SUMMARY OF THE INVENTION

The object of the present invention is to provide a process to fractionate lignocellulosic material into three product streams, each derived from a major lignocellulose constituent, being cellulose, lignin, and hemicellulose.

A first aspect of the present invention relates to the treatment of lignocellulosic material in a liquid medium comprising water and an alcohol solvent. In one embodiment of the invention, the alcohol solvent is not fully miscible with water at room temperature.

Another aspect of the invention relates to the utilisation of a catalyst based on a transition metal based on ruthenium or nickel to catalytically convert solubilised lignin and solubilised polysaccharides. Solubilised lignin is catalytically converted towards a mixture of low M, phenolic compounds, including monophenolic compounds such as 4-(3-hydroxy-propyl)-guaiacol, 4-(3-hydroxy-propyl)-syringol, 4-n-propylguaiacol, 4-n-propylsyringol. Solubilised polysaccharides are catalytically converted into polyols such as xylitol and sorbitol, as well as oligomers. The cellulose fraction is retained as a polymer in a solid residue.

Another aspect of the invention relates to the high and tuneable selectivity towards certain substitution patterns (such as 4-(3-hydroxy-propyl) groups) on the obtained phenolic compounds. The selectivity of monomers with a 4-(3-hydroxy-propyl) group is higher than 60 wt % relative to the total amount of monomers, such as 80 wt %.

Another aspect of the invention relates to the separation of the cellulosic pulp by means of filtration.

Another aspect of the invention relates to the separation of phenolic compounds from carbohydrate-derived compounds by means of liquid-liquid extraction utilising a biphasic solvent system.

In a specific embodiment the present invention concerns, catalytic lignocellulose biorefining in alcohol/water, for instance n-butanol/water: a one-pot approach toward phenolics, polyols, and cellulose. A process to convert lignocellulosic material into (i) lignin-derived phenolic compounds, (ii) hemicellulose-derived polyols and oligomers, and (iii) a cellulosic pulp by treating lignocellulosic material in presence of a nickel- or ruthenium-based catalyst under reducing atmosphere, for instance a hydrogen atmosphere. The invention further relates to separation of the product streams obtainable by the process.

Another object of present invention is to provide a chemo-catalytic biorefinery to convert lignocellulosic biomass (such as *Eucalyptus* sawdust) into (i) lignin-derived phenolics, (ii) hemicellulose-derived polyols, and (iii) a cellulose pulp. This can be achieved by processing biomass in a mixture of alcohol and water (e.g. n-butanol/water) at elevated temperature (e.g. 200° C.), in the presence of Ru- or Ni-based catalyst, and pressurised hydrogen (e.g. 30 bar, at room temperature). During this one-pot Reductive Catalytic Fractionation (RCF) process, the hot liquor enables the extraction and solvolytic depolymerisation of both lignin and hemicellulose, while the catalyst and reductive environment support the hydrogenation of unstable intermediates (coniferyl/sinapyl alcohol and sugars) toward stable target products (propanol-substituted guaiacols/syringols and polyols, respectively). After the catalytic reaction, the solid carbohydrate pulp (mainly cellulose) is easily retrieved upon filtration. Phase separation of n-butanol and water occurs below 125° C., which offers a facile and effective strategy to isolate lignin-derived phenolics (n-butanol phase) from polyols (aqueous phase). The three resulting product streams provide a versatile platform for down-stream conversion, and route to bio-based chemicals. Such processes are easy to scale up. For instance in a proof-of-concept experiment using a 2 L batch reactor demonstrates the scalability potential. Furthermore, this contribution highlights that the conversion of each biopolymer is influenced in a different way by reaction parameters like catalyst, hydrogen pressure, temperature, and/or acidity (HCl). The process output is tuneable, by tuning of temperature, reaction time, polarity of the liquid medium, and acidity of the medium. These parameters govern the process 'severity', and determine to what extent the biomass constituents are solubilized and converted.

In a particular aspect the invention provides a method for preparing or transforming lignocellulosic material into a liquid mixture of phenolic compounds, a liquid mixture sugar-derived polyols and oligosaccharides and a solid cellulose, by subjecting lignocellulosic material to a treatment at a temperature of at least 150° C., in a biphasic solvent system, preferably such solvent comprising water and an organic solvent for which the upper critical solution temperature is lower than the treatment temperature such as alcohol, in the presence of a nickel and/or ruthenium catalyst and externally supplied hydrogen source for instance for a reaction time of 0.05-12 hours by further removing the solid cellulosic material and cooling the solvent system below the upper critical solution temperature or cooling the solvent system below the upper critical solution temperature and thereafter removing the solid cellulosic material and by separating the mono-, di-, polyphenolic molecules from the sugar-derived polyols and oligosaccharides by performing liquid-liquid extraction using the biphasic solvent system. In this method the lignocellulosic material and biphasic solvent (reaction phase) can be in a separated reaction vessel than the catalyst in biphasic solvent (catalytic phase) whereby reaction product of the reaction phase is transferred to the reaction vessel of the catalytic phase. Or alternatively the lignocellulosic material and the catalyst under hydrogen gas are together in biphasic solvent in one reaction vessel. Such method of this particular embodiment is particularly suitable for transforming hardwood, lignocellulosic material that is at least 50% hardwood, lignocellulosic material that is at least 80% hardwood, lignocellulosic material that comprises hardwood, softwood, herbaceous biomass, straw, bark, waste wood, flax shives, sugar cane bagasse, corn stover or crop residues to manufacture liquid mixture of phenolic compounds, a liquid mixture sugar-derived polyols and oligosaccharides and a solid cellulose restreams. Such method works at reaction temperature on the lignocellulosic material in the biphasic solvent of water and alcohol and on the catalyst in the biphasic solvent of water and alcohol under a hydrogen atmosphere being in the range of 150° C. to 260° C., preferably the reaction temperature is in the range of 170° C. to 225° C. and yet more preferably in the range of 180° C. to 210° C. Such method can operate in a one step process, for instance it can be characterised in that it fractionation of lignocellulosic material and depolymerisation of solubilised lignin and polysaccharides into a biphasic solvent system and a solid fraction is a one step process. It is most practical to have the solid cellulosic material removed by filtration. This embodiment of the invention advantageously comprises a mixture of water and an alcohol as biphasic solvent system; for instance a mixture of water and an alcohol of the group consisting of 1-butanol, 1-pentanol, iso-amylalcohol, and 1-hexanol or a mixture thereof. It is most practical to have the supplied hydrogen source as pressurised hydrogen gas. In an advantageous embodiment, the method according to the present invention further comprises that the solvent-to-water ratio is in the range of 20:80 and 80:20 on a volumetric basis. In an advantageous embodiment, the method according to the present invention further comprises adding additionally an acid catalyst (for instance a mineral acid catalyst of the group consisting of hydrochloric acid, sulphuric acid and phosphoric acid or a carboxylic acid such as acetic acid or a wherein a sulfonic acid such as triflic acid catalyst or a Lewis acid catalyst such as Ni(II)-triflate, Cu(II)-triflate, Al(III)-triflate, Yb(III)-triflate, Sc(III)-triflate, La(III)-triflate, Hf(IV)-triflate) or a base catalyst to the solvent system prior to the treatment. In an advantageous embodiment, the concentration of the acid catalyst in the solvent system is in the range of 0.1 mM and 25 mM.

With respect to the hydrogen gas, it is noted that it is advantageous if the hydrogen pressure is between 5 and 50 bar at room temperature.

By using the method of this invention it is possible that the combined isolated yield of sugar-derived polyols and oligosaccharides is higher than 50 wt %.

This embodiment of the invention advantageously also comprises that the cellulose retention of the pulp is higher than 75 wt %. In another aspect, the cellulose content of the obtained pulp is preferably higher than 80 wt %.

In another aspect, the method present invention provides that one or more phenolic molecules have the formula of:

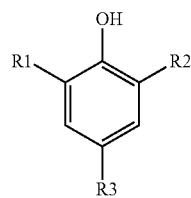

wherein each R1 and R2 is —H, —OH or —OCH$_3$
and R3 is —CH$_2$CH$_3$, —(CH$_2$)$_2$CH$_3$, —(CH)$_2$CH$_3$, —CH$_2$CHCH$_2$, or —(CH$_2$)$_2$CH$_2$OH.

In yet another aspect, the method present invention provides that the yield of the monophenolic molecules is higher than 20 wt % relative to the lignin content of the parent lignocellulosic material.

In yet another aspect, the method of the present invention provides that one or more diphenolic molecules have the formula of:

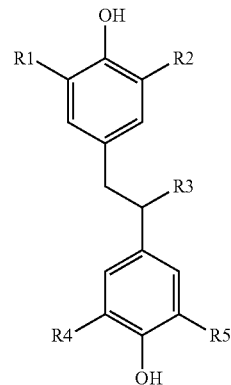

wherein each R1, R2, R4 and R5 is —H, —OH or —OCH$_3$
and R3 is —H, —CH$_3$ or —CH$_2$OH In yet another aspect, the method of the present invention provides that one or more diphenolic molecules have the formula of:

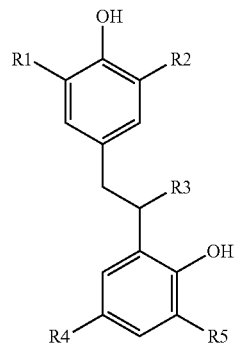

wherein each R1, R2 and R5 is —H, —OH or —OCH$_3$
and R3 is —H, —CH$_3$ or —CH$_2$OH
and R4 is —CH$_2$CH$_3$, —(CH$_2$)$_2$CH$_3$, —(CH)$_2$CH$_3$, —CH$_2$CHCH$_2$, or —(CH$_2$)$_2$CH$_2$OH In yet another aspect, the method of the present invention provides that one or more diphenolic molecules have the formula of:

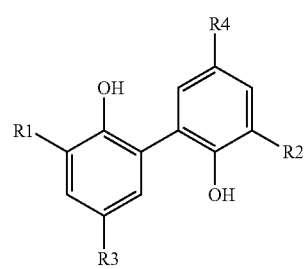

wherein each R1 and R2 is —H, —OH or —OCH$_3$
and each R3 and R4 is —CH$_2$CH$_3$, —(CH$_2$)$_2$CH$_3$, —(CH)$_2$CH$_3$, —CH$_2$CHCH$_2$, or —(CH$_2$)$_2$CH$_2$OH.

In yet another aspect, the method of the present invention provides that one or more sugar-derived polyols comprise xylitol, arabitol, dulcitol, mannitol, sorbitol, ethylene glycol, 1,2-propylene glycol, 1,3-propylene glycol, glycerol.

In yet another aspect, the method of the present invention provides that more than 60 wt % of the obtained sugar-derived polyols comprise C5 polyols and C6 polyols, such as more than 80 wt %.

In yet another embodiment of the invention, is provided a mixture comprising a lignocellulose substrate or lignocellulose substrates in the form of powder, particles or granules in a biphasic solvent system comprising water and an alcohol and further metal catalyst is based on ruthenium or nickel and further comprising an acid catalyst or a base catalyst, the mixture being at a temperature between 170° C. and 225° C. and under hydrogen pressure.

In yet another embodiment of the invention, is provided three separate, separable or self-separating fractions 1) phenolic product mixture with weight average molecular weight of not more than 1500 g·mol$^{-1}$, comprising monophenolic molecules, diphenolic molecules, and polyphenolic molecules, 2) aqueous mixture of sugar-derived polyols and oligosaccharides and 3) solid product comprising more than 50 wt % of cellulosic material; obtained from the mixture comprising a lignocellulose substrate or lignocellulose substrates in the form of powder, particles or granules in a biphasic solvent system comprising water and an organic solvent and further metal catalyst is based on ruthenium, platinum or nickel and further comprising an acid catalyst or a base catalyst, the mixture being at a temperature between 170° C. and 225° C. and under hydrogen pressure and obtained after a reaction time of 0.05-12 hours.

In yet another embodiment of the invention, is provided an isolated phenolic product mixture with weight average molecular weight of not more than 1500 g·mol$^{-1}$, comprising monophenolic molecules, diphenolic molecules, and polyphenolic molecules, obtained from the mixture comprising a lignocellulose substrate or lignocellulose substrates in the form of powder, particles or granules in a biphasic solvent system comprising water and an organic solvent and further metal catalyst is based on ruthenium, platinum or nickel and further comprising an acid catalyst or a base catalyst, the mixture being at a temperature between 170° C. and 225° C. and under hydrogen pressure and obtained after a reaction time of 0.05-12 hours.

In yet another embodiment of the invention, is provided an isolated phenolic product mixture wherein one or more phenolic molecules have the formula of:

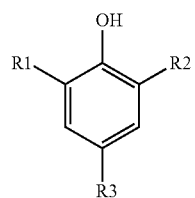

wherein each R1 and R2 is —H, —OH or —OCH$_3$
and R3 is —CH$_2$CH$_3$, —(CH$_2$)$_2$CH$_3$, —(CH)$_2$CH$_3$, —CH$_2$CHCH$_2$, or —(CH$_2$)$_2$CH$_2$OH; obtained from the mixture comprising a lignocellulose substrate or lignocellulose substrates in the form of powder, particles or granules in a biphasic solvent system comprising water and an organic solvent and further metal catalyst is based on ruthenium, platinum or nickel and further comprising an acid catalyst or a base catalyst, the mixture being at a temperature between 170° C. and 225° C. and under hydrogen pressure and obtained after a reaction time of 0.05-12 hours.

In yet another embodiment of the invention, is provided one or more diphenolic molecules have the formula of:

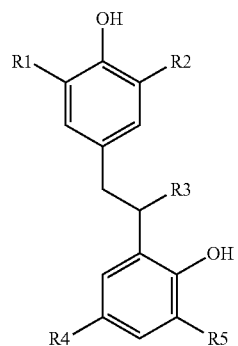

wherein each R1, R2 and R5 is —H, —OH or —O—CH$_3$
and R3 is —H, —CH$_3$ or —CH$_2$OH
and R4 is —CH$_2$CH$_3$, —(CH$_2$)$_2$CH$_3$, —(CH)$_2$CH$_3$, —CH$_2$CHCH$_2$, or —(CH$_2$)$_2$CH$_2$OH; obtained from the mixture comprising a lignocellulose substrate or lignocellulose substrates in the form of powder, particles or granules in a biphasic solvent system comprising water and an organic solvent and further metal catalyst is based on ruthenium, platinum or nickel and further comprising an acid catalyst or a base catalyst, the mixture being at a temperature between 170° C. and 225° C. and under hydrogen pressure and obtained after a reaction time of 0.05-12 hours.

In yet another embodiment of the invention, is provided isolated phenolic product mixture, wherein one or more diphenolic molecules have the formula of:

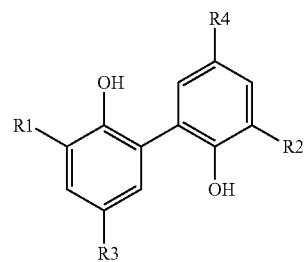

wherein each R1 and R2 is —H, —OH or —OCH$_3$
and each R3 and R4 is —CH$_2$CH$_3$, —(CH$_2$)$_2$CH$_3$, —(CH)$_2$CH$_3$, —CH$_2$CHCH$_2$, or —(CH$_2$)$_2$CH$_2$OH; obtained from the mixture comprising a lignocellulose substrate or lignocellulose substrates in the form of powder, particles or granules in a biphasic solvent system comprising water and an organic solvent and further metal catalyst is based on ruthenium, platinum or nickel and further comprising an acid catalyst or a base catalyst, the mixture being at a temperature between 170° C. and 225° C. and under hydrogen pressure and obtained after a reaction time of 0.05-12 hours.

In yet another embodiment of the invention, is provided an isolated aqueous mixture of sugar-derived polyols and oligosaccharides obtained from the mixture comprising a lignocellulose substrate or lignocellulose substrates in the form of powder, particles or granules in a biphasic solvent system comprising water and an organic solvent and further metal catalyst is based on ruthenium, platinum or nickel and further comprising an acid catalyst or a base catalyst, the mixture being at a temperature between 170° C. and 225° C. and under hydrogen pressure and obtained after a reaction time of 0.05-12 hours.

In yet another embodiment of the invention, is provided an isolated solid product comprising more than 50 wt % of cellulosic material obtained from the mixture comprising a lignocellulose substrate or lignocellulose substrates in the form of powder, particles or granules in a biphasic solvent system comprising water and an organic solvent and further metal catalyst is based on ruthenium, platinum or nickel and further comprising an acid catalyst or a base catalyst, the mixture being at a temperature between 170° C. and 225° C. and under hydrogen pressure and obtained after a reaction time of 0.05-12 hours.

BRIEF DESCRIPTION OF THE DRAWINGS

The present invention will become more fully understood from the detailed description given herein below and the accompanying drawings which are given by way of illustration only, and thus are not limitative of the present invention, and wherein:

FIGS. 24-2D demonstrate the analysis of the n-butanol phase and aqueous phase obtained from Ru/C-catalysed RCF of eucalyptus. Reaction scheme see FIG. 1. Reaction conditions (see also EXAMPLE 1): 20 mL water, 20 mL n-butanol, 0.2 g Ru/C, 2 g Eucalyptus sawdust, 200° C. 2 h, 30 bar $H_2$. (FIG. 2A) Lignin monomer yield, expressed as mg monomers per g biomass. (FIG. 2B) Yield of sugar products in aqueous phase, expressed as mg per g biomass, (FIG. 2C) GPC analysis. Signal assignment is based on analytical standards and self-synthesised dimers and trimers (Fig. S10). (FIG. 2D) HSQC NMR. The presence of trace amounts of polyols is due to repeated extraction of the aqueous phase n-butanol (3 cycles), but can be mninimised by optimisation of the extraction procedure.

(FIG. 8A) Yield of lignin monomers in n-butanol phase and (FIG. 8B) carbohydrate monomer products in aqueous phase. For each reaction temperature (160, 180 and 200° C.), a different acidity range was investigated. Reaction conditions: 2 g Eucalyptus, 0.2 g Ru/C, 20 mL water, 20 mL n-butanol, 2 h, 30 bar $H_2$. The n-butanol oil yield or degree of hemicellulose solubilisation is displayed on the secondary y-axis.

FIG. 11A shows the obtained yield of monophenolics. FIG. 11B shows the obtained yield of monomeric sugar-derivatives, analysed by GC. FIG. 11C shows the yield of sugar-derived products, including the hemicellulose-derived oligomers. Reaction conditions: 20 mL water, 20 mL n-butanol, 0.2 g Ru/C, 2 g Eucalyptus sawdust, 30 bar $H_2$.

DETAILED DESCRIPTION OF THE INVENTION

Figure 1:
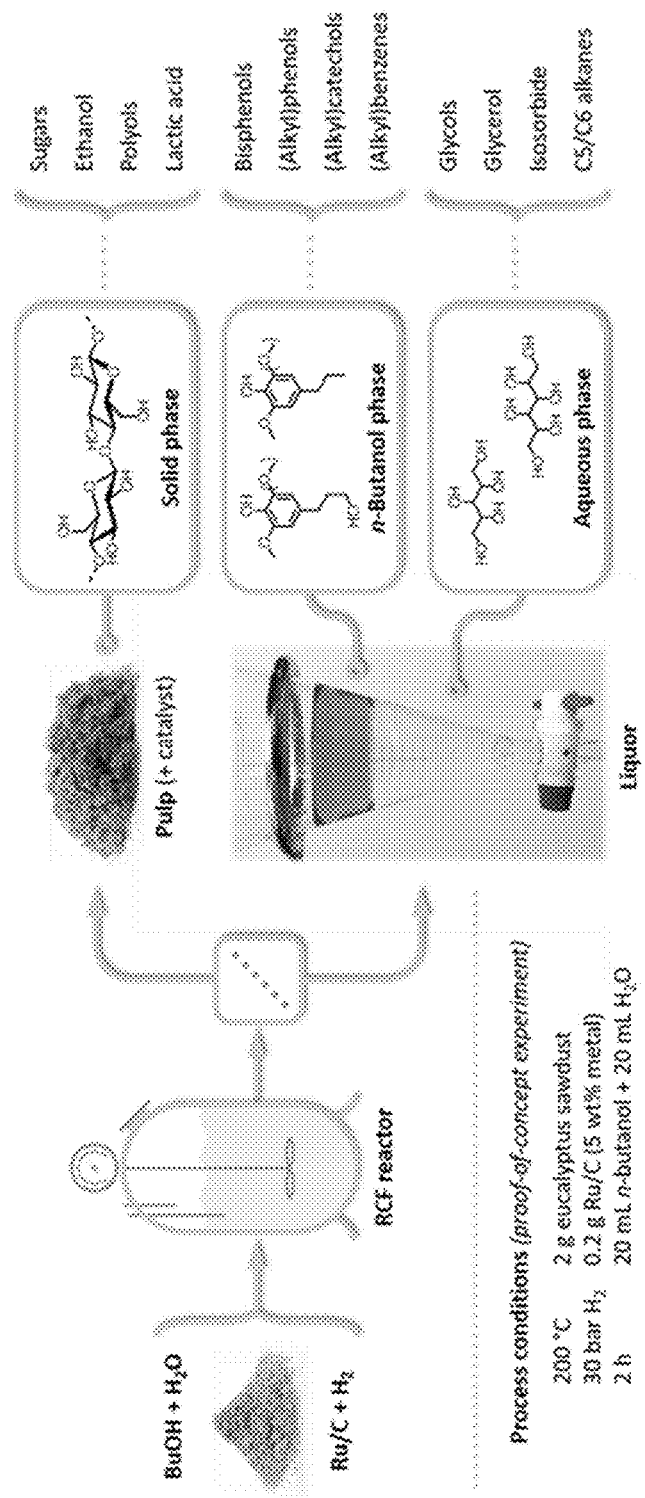
FIG. 1 is a general scheme of the process of the invention, using a mixture of n-butanol and water, targeting (i) a cellulosic pulp, (ii) lignin-derived phenolies, and (iii) hemicellulose-derived polyols. The n-butanol/water processing liguor is monophasic during the reaction (200° C.), but biphasic below 125° C. For each product stream, a few valorisation opportunities are presented.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description. It is to be understood that both the foregoing general description and the following detailed description are exemplary and explanatory only and are not restrictive of the invention, as claimed.

Definitions and Introduction

In the present invention, the term "biomass" is used for the term "lignocellulosic material" and lignocellulosic material may be in the meaning of lignocellulose or material comprising lignocellulose.

In the present invention, the term "monophenolic compounds" means molecules with one phenolic group. The molecules result from the chemical modification of lignin. Hence they are referred to as "lignin-derived monophenolics", "lignin-derived monomers", "lignin monomers", or "phenolic monomers". These terms are used interchangeably. Chemical modification herein means depolymerisation and/or partial reduction. The lignin-derived monophenolics comprise compounds having the formula of:

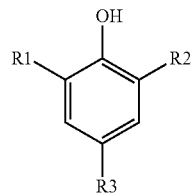

wherein each R1 and R2 is —H, —OH or —OCH$_3$ and R3 is —CH$_2$CH$_3$, —(CH$_2$)$_2$CH$_3$, —(CH)$_2$CH$_3$, —CH$_2$CHCH$_2$, or —(CH$_2$)$_2$CH$_2$OH.

Phenolic monomers wherein R1 is —H and R2 is —OCH$_3$ are referred to as guaiacols, abbreviated with G. Phenolic monomers wherein R1 is —OCH$_3$ and R2 is —OCH$_3$ are referred to as syringols, abbreviated with S. Phenolic monomers wherein R3 is —CH$_2$CH$_3$ are referred to as ethyl-substituted monomers. Phenolic monomers wherein R3 is —(CH$_2$)$_2$CH$_3$ are referred to as propyl-substituted monomers. Phenolic monomers wherein R3 is —(CH$_2$)$_2$CH$_2$OH are referred to as propanol-substituted monomers. Phenolic monomers wherein R3 is —(CH)$_2$CH$_3$ or —CH$_2$CHCH$_2$ are referred to as unsaturated monomers. Specific examples of said phenolic monomers are:

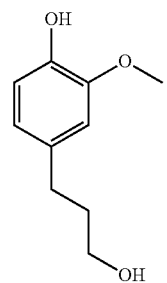

(1)

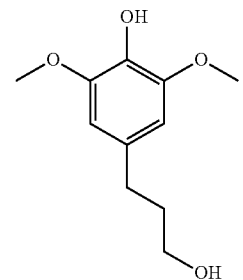

(2)

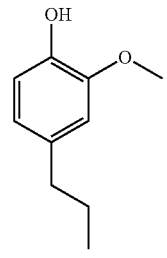

(3)

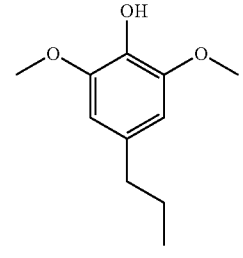

(4)

(1) is referred to as "4-(3-hydroxy-propyl)-guaiacol", "propanol-guaiacol", or simply "propanol-G"
(2) is referred to as "4-(3-hydroxy-propyl)-syringol", "propanol-syringol", or simply "propanol-S"
(3) is referred to as "4-n-propyl-guaiacol", "propyl-guaiacol", or simply "propyl-G"

(4) is referred to as "4-n-propyl-syringol", "propyl-syringol", or simply "propyl-S"

In the present invention, the term "diphenolic compounds" means molecules with two phenolic centres chemically linked to each other. The molecules result from the chemical modification of lignin. Hence they are referred to as "lignin-derived diphenolics", "lignin-derived dimers", or "phenolic dimers". These terms are used interchangeably. Chemical modification herein means depolymerisation and/or partial reduction. The lignin-derived dimers comprise compounds having the formula of:

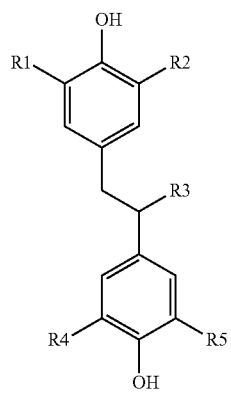

wherein each R1, R2, R4 and R5 is —H, —OH, or —OCH₃
and R3 is —H, —CH₃ or —CH₂OH;

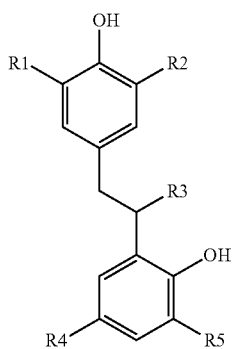

wherein each R1, R2 and R5 is —H, —OH or —OCH₃
and R3 is —H, —CH₃ or —CH₂OH
and R4 is —CH₂CH₃, —(CH₂)₂CH₃, —(CH)₂CH₃, —CH₂CHCH₂, or —(CH₂)₂CH₂OH;

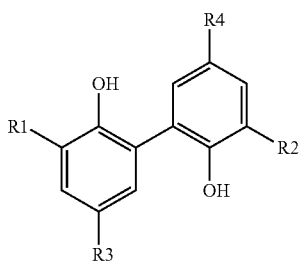

wherein each R1 and R2 is —H, —OH or —OCH₃
and each R3 and R4 is —CH₂CH₃, —(CH₂)₂CH₃, —(CH)₂CH₃, —CH₂CHCH₂, or —(CH₂)₂CH₂OH;

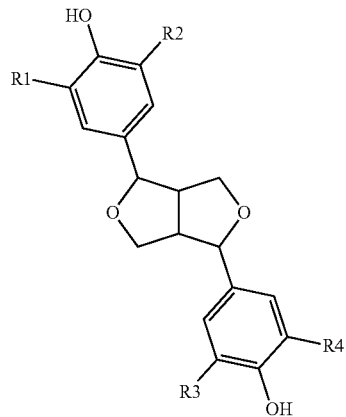

wherein each R1, R2, R3 and R4 is —H, —OH or —OCH₃;

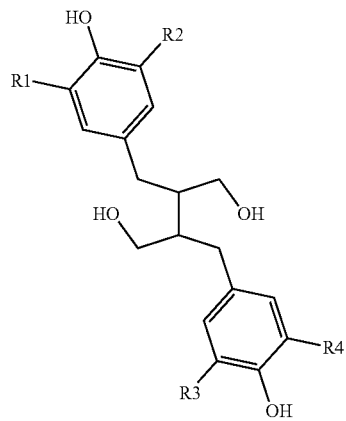

wherein each R1, R2, R3 and R4 is —H, —OH or —OCH₃.

In the present invention, the term "polyphenolic compounds" means molecules with more than two phenolic centres chemically linked to each other. The molecules result from the chemical modification of lignin. Hence they are referred to as "lignin-derived polyphenolics", "lignin-derived oligomers", or "phenolic oligomers". These terms are used interchangeably. Chemical modification herein means depolymerisation and/or partial reduction.

In the present invention, the term "phenolic compounds" and "phenolic products mixture" are used interchangeably to indicate the mixture comprising monophenolic compounds, diphenolic compounds, and phenolic oligomers.

In the present invention, the term "hemicellulose-derived polyols" or simply "polyols" means aliphatic alcohols comprising at least two hydroxyl groups. In the present invention, the term "hemicellulose-derived polyols" or "polyols" does not include monosaccharides or oligosaccharides. Hemicellulose-derived polyols include sugar alcohols derived from hydrogenation of monosaccharides. The polyols result from the chemical modification of hemicellulose. Chemical modification herein means hydrolysis and hydrogenation. Hemicellulose-derived polyols primarily include xylitol, arabitol, dulcitol, mannitol, sorbitol, ethylene glycol, glycerol. The term "C5 polyols" is used to indicate the group of polyols comprising 5 carbon atoms, such as xylitol and arabitol. The term "C6 polyols" is used to indicate the group of polyols comprising 6 carbon atoms, such as dulcitol, mannitol, and sorbitol. Likewise, the term "C5 sugars" is used to indicate the group of sugars comprising 5 carbon atoms, such as xylose and arabinose. The term "C6 sugars" is used to indicate the group of sugars comprising 6 carbon atoms, such as glucose, mannose, and galactose.

The term "hemicellulose-derived oligosaccharides", "hemicellulose oligomers" or simply "oligosaccharides" is used to indicate molecules comprising two or more saccharide monomers or saccharide-derived monomers, linked to each other by a glycosidic bond. The term "oligosaccharides" is used to denote saccharide oligomers with a non-reduced terminal saccharide group as well as molecules with a reduced terminal saccharide group. Examples of such oligosaccharides include, but are not limited to,

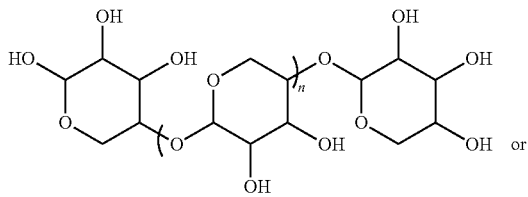

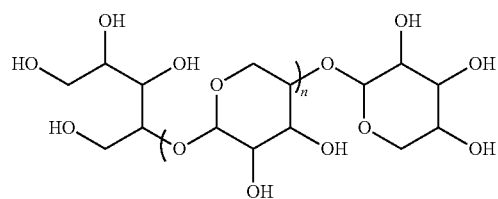

with n between 0-7, for example 0-3.

The term "unstable compounds" is used to refer to compounds that are unstable under the reaction conditions, and that cause unwanted side-reactions, such as recondensation. Unstable compounds typically bear a C=O or C=C functional group. Examples of such unstable compounds derived from carbohydrates include, but are not limited to, xylose, glucose, furfural, and hydroxymethylfurfural. Examples of unstable compounds derived from lignin include, but are not limited to, coniferyl alcohol, sinapyl alcohol, phenolic compounds with C2-aldehyde substituents, and so-called Hibbert's ketones. These unstable compounds can be transformed to "stable compounds" by transforming the C=O and/or C=C functional groups, for instance through hydrogenation. The term "stable compounds" is used to refer to compounds that are stable under the reaction conditions, and that do not cause unwanted side-reactions, such as recondensation. Examples of stable compounds derived from carbohydrates include, but are not limited to, xylitol, arabitol, dulcitol, mannitol, sorbitol, ethylene glycol, glycerol. Examples of stable compounds derived from lignin include, but are not limited to, 4-n-propanolsyringol, 4-n-propanolguaiacol, 4-n-propylsyringol, 4-n-propylguaiacol.

"n-Butanol" or simply "butanol" is abbreviated as "BuOH".

"Methanol" is abbreviated as "MeOH".

"Ethanol" is abbreviated as "EtOH".

According to one embodiment the invention concerns a process of producing polyols and phenolic compounds, the process comprising subjecting to a temperature of at least 150° C. of A) a feedstock medium comprising water and alcohol and feedstock of lignocellulosic material and B) a catalytic medium comprising water and alcohol, hydrogen gas, and a catalyst comprising ruthenium and/or nickel or it concerns a process for producing polyols and phenolic compounds, the process comprising combining lignocellulose, a lignocellulosic material or a feedstock comprising lignocellulose with a) water and alcohol, b) a catalyst comprising ruthenium and/or nickel and c) hydrogen gas and subjecting these to a temperature of at least 150° C.

This process of producing polyols and phenolic compounds described above may be embodied as A) subjecting a lignocellulose, lignocellulosic material or a feedstock comprising lignocellulose in a medium of water and alcohol to a temperature of at least 150° C., B) subjecting to a temperature of at least 150° C. a medium comprising ruthenium and/or nickel catalyst in a water and alcohol under an hydrogen atmosphere and C) supplying the reaction product of the processed lignocellulosic material to the catalyst medium. These embodiments of the invention advantageously comprises that the catalytic medium is pressurized under hydrogen gas. The catalytic medium may receive the hydrogen gas from an external source.

In a particular embodiment of the present invention, the feedstock medium and the catalytic medium are in two separated vessels. In yet another particular embodiment of present invention the feedstock medium and the catalytic medium are combined in the same vessel. In another aspect, the present invention provides that the reaction vessel is pressurized under the hydrogen gas or the reaction vessels are pressurized under the hydrogen gas. By using an inventive method described above it is possible to produce 1) a mixture of mono-, di- and polyphenolic compounds, 2) a mixture of sugar-derived polyols and oligosaccharides and 3) a solid, cellulose-enriched material.

Some of the methods described above may be embodied as that the externally supplied hydrogen gas is at a partial pressure of 5 bar or higher at room temperature or said externally supplied hydrogen gas is at a partial pressure of 10 bar or higher at room temperature or that the externally supplied hydrogen gas is at a partial pressure between 10 and 30 bar at room temperature so that the percentage by mass of monophenolic compounds in said mixture of mono-, di- and polyphenolic compounds, is between 20% and 100%.

Some of the methods described above may be embodied as that the externally supplied hydrogen gas is at a partial pressure of 5 bar or higher at room temperature or that the supplied hydrogen gas is at a partial pressure of 10 bar or higher at room temperature or that the externally supplied hydrogen gas is at a partial pressure between 10 and 30 bar at room temperature so that the yield of monophenolic compounds is between 12% and 60%, such as between 20 and 50%, on mass basis relative to the lignin content of the used lignocellulosic material.

Some of the methods described above may be embodied as that the externally supplied hydrogen gas is at a partial pressure of 10 bar or higher at room temperature or that the externally supplied hydrogen gas is at a partial pressure between 10 and 30 bar at room temperature so that more than 60% by mass of the monophenolic compounds in said mixture of phenolic compounds, comprises a compound having the general formula

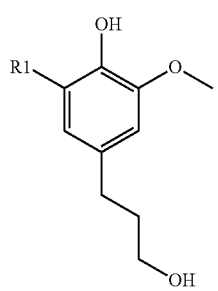

wherein R1 is —H, —OH or —OCH$_3$

Some of the methods described above may be embodied as that the externally supplied hydrogen gas is at a partial pressure of 10 bar or higher at room temperature or that the externally supplied hydrogen gas is at a partial pressure between 10 and 30 bar at room temperature so that the mixture of phenolic mono-, di- and polyphenolic compounds has an aliphatic OH content being higher than 3 mmol aliphatic OH-groups per gram of said mixture, such higher than 4 mmol aliphatic OH-groups per gram of said mixture.

Some of the methods described above may be embodied as that the externally supplied hydrogen gas is at a partial pressure of 5 bar or higher at room temperature or that the externally supplied hydrogen gas is at a partial pressure of 10 bar or higher at room temperature so that said mixture of mono-, di-, polyphenolic compounds, has an average molecular weight of not more than 1500 g/mol.

Some of the methods described above may be embodied as that the externally supplied hydrogen gas is at a partial pressure of 10 bar or higher at room temperature or that the externally supplied hydrogen gas is at a partial pressure between 10 and 30 bar at room temperature so that the combined yield of sugar-derived polyols and oligosaccharides is higher than 50% by mass relative to the hemicellulose content of said lignocellulosic material.

Some of the methods described above may be embodied as that the externally supplied hydrogen gas is at a partial pressure of 5 bar or higher at room temperature or that the externally supplied hydrogen gas is at a partial pressure of 10 bar or higher at room temperature so that the polyols are of the group of xylitol, arabitol, dulcitol, mannitol, sorbitol, ethylene glycol, 1,2-propylene glycol, 1,3-propylene glycol and glycerol or mixtures thereof.

Some of the methods described above may be embodied as that the externally supplied hydrogen gas is at a partial pressure of 10 bar or higher, or that the externally supplied hydrogen gas is at a partial pressure between 10 and 30 bar at room temperature and wherein more than 80% by mass of the monophenolic compounds in said mixture phenolic compounds, comprises a compound having the general formula

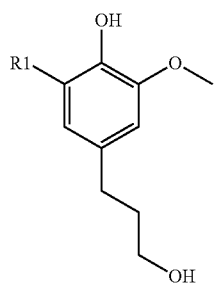

wherein R1 is —H, —OH or —OCH$_3$

A process according to any one of the claims 1 to 13 wherein the percentage by mass of said mono-, di- and polyphenolic compounds relative to the total lignin content of said lignocellulosic material, is higher than 35%.

In one embodiment of the invention, the catalyst comprises Ru on carbon.

In a further embodiment of present invention the mono-, di-, polyphenolic molecules are separated from the sugar-derived polyols and oligosaccharides by performing liquid-liquid extraction.

In a further embodiment of present invention the liquid medium comprises a mixture of water and an alcohol of the group consisting of methanol, ethanol, 2-propanol, 2-methyl-propanol, ethylene glycol and glycerol, or a mixture thereof.

In a further embodiment of present invention the liquid medium comprising water and alcohol solvent is a biphasic mixture when below 100° C.

In a further embodiment of present invention the alcohol solvent is of the group of 1-butanol, 1-pentanol, 2-pentanol, 3-methylbutan-1-ol and 2-ethyl hexan-1-ol, or a mixture thereof.

In a further embodiment of present invention the mono-, di-, polyphenolic molecules are separated from said sugar-derived polyols and oligosaccharides by performing liquid-liquid extraction using said liquid medium comprising water and alcohol solvent.

In a further embodiment of present invention the lignocellulosic material comprises hardwood, softwood, herbaceous biomass, straw, bark, waste wood, flax shives, sugar cane bagasse, corn stover or crop residues.

In a further embodiment of present invention the lignocellulosic material is wood biomass. In a further embodiment of present invention the lignocellulosic material is hardwood.

In a further embodiment of present invention the lignocellulosic material is at least 50% hardwood.

In a further embodiment of present invention the lignocellulosic material is at least 80% hardwood.

In a further embodiment of present invention the temperature is in the range of 150° C. to 240° C.

In a further embodiment of present invention the temperature is in the range of 170° C. to 220° C.

In a further embodiment of present invention the temperature is in the range of 180° C. to 210° C.

In a further embodiment of present invention the reaction time is in the range of 0.05-12 hours, more preferably in the range of 0.5-6 h.

In a further embodiment of present invention the cellulose-enriched material is removed by filtration.

In a further embodiment of present invention the ratio of alcohol solvent to water is in the range of 20:80 and 80:20 on a volumetric basis.

In a further embodiment of present invention the ratio of alcohol solvent to water is in the range of 40:60 and 60:40 on a volumetric basis.

In a further embodiment of present invention the catalyst is spatially separated from said lignocellulosic material.

In a further embodiment of present invention additionally to catalyst an acid catalyst is added to said liquid medium prior to the treatment.

In a further embodiment of present invention the concentration of the acid catalyst in the solvent system is in the range of 0.1 mM and 25 mM.

In a further embodiment of present invention the acid catalyst is a mineral acid catalyst.

In a further embodiment of present invention the mineral acid catalyst of the group consisting of hydrochloric acid, sulphuric acid and phosphoric acid, or a mixture thereof.

In a further embodiment of present invention the he acid catalyst is a carboxylic acid catalyst.

In a further embodiment of present invention the carboxylic acid catalyst is formic acid, acetic acid, or a mixture thereof.

In a further embodiment of present invention the acid catalyst is a sulfonic acid catalyst is added to said liquid medium prior to the treatment.

In a further embodiment of present invention additionally to catalyst a Lewis acid catalyst of the group of $AlCl_3$, $ZnCl_2$, $FeCl_3$, Ni(II)-triflate, Cu(II)-triflate, Al(III)-triflate, Yb(III)-triflate, Sc(III)-triflate, La(III)-triflate and Hf(IV)-triflate, or a mixture thereof is added to said liquid medium prior to the treatment.

In a further embodiment of present invention the cellulose content of said cellulose-enriched pulp is higher than 50%.

In a further embodiment of present invention the cellulose content of said cellulose-enriched pulp is higher than 85 wt %.

In a further embodiment of present invention one or more phenolic molecules have the general formula of:

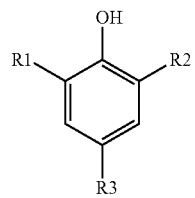

wherein each R1 and R2 is —H, —OH or —OCH₃ and R3 is —CH₂CH₃, —(CH₂)₂CH₃, —(CH)₂CH₃, —CH₂CHCH₂, or —(CH₂)₂CH₂OH.

In a further embodiment of present invention one or more diphenolic molecules have the general formula of:

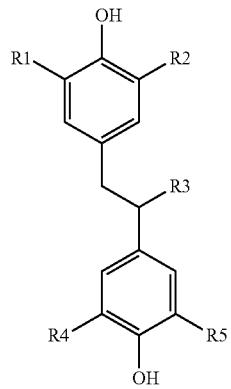

wherein each R1, R2, R4 and R5 is —H, —OH, or —OCH₃ and R3 is —H, —CH₃ or —CH₂OH In a further embodiment of present invention one or more diphenolic molecules have the general formula of:

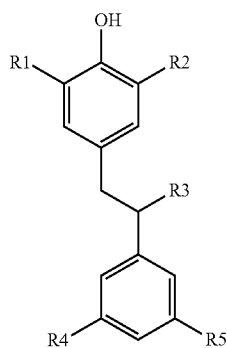

wherein each R1, R2 and R5 is —H, —OH or —O—CH₃ and R3 is —H, —CH₃ or —CH₂OH
and R4 is —CH₂CH₃, —(CH₂)₂CH₃, —(CH)₂CH₃, —CH₂CHCH₂, or —(CH₂)₂CH₂OH In a further embodiment of present invention one or more diphenolic molecules have the general formula of:

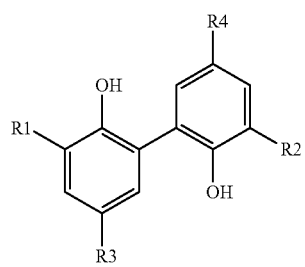

wherein each R1 and R2 is —H, —OH or —OCH₃
and each R3 and R4 is —CH₂CH₃, —(CH₂)₂CH₃, —(CH)₂CH₃, —CH₂CHCH₂, or —(CH₂)₂CH₂OH.

In a further embodiment of present invention one or more diphenolic molecules have the general formula of:

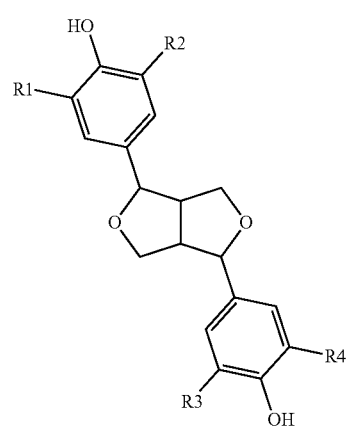

wherein each R1, R2, R3 and R4 is —H, —OH or —OCH₃

In a further embodiment of present invention one or more diphenolic molecules have the general formula of:

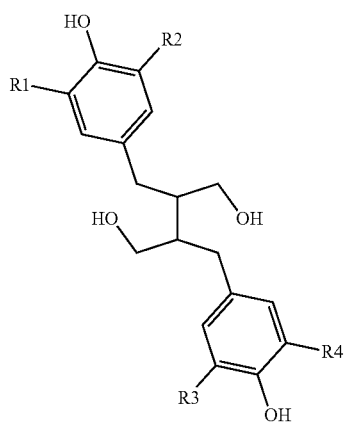

wherein each R1, R2, R3 and R4 is —H, —OH or —OCH$_3$

The following detailed description of the invention refers to the accompanying drawings. The same reference numbers in different drawings identify the same or similar elements. Also, the following detailed description does not limit the invention. Instead, the scope of the invention is defined by the appended claims and equivalents thereof.

Several documents are cited throughout the text of this specification. Each of the documents herein (including any manufacturer's specifications, instructions etc.) are hereby incorporated by reference; however, there is no admission that any document cited is indeed prior art of the present invention.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn to scale for illustrative purposes. The dimensions and the relative dimensions do not correspond to actual reductions to practice of the invention.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to the devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Other embodiments of the invention will be apparent to those skilled in the art from consideration of the specification and practice of the invention disclosed herein.

It is intended that the specification and examples be considered as exemplary only.

Each and every claim is incorporated into the specification as an embodiment of the present invention. Thus, the claims are part of the description and are a further description and are in addition to the preferred embodiments of the present invention.

Each of the claims set out a particular embodiment of the invention.

The following terms are provided solely to aid in the understanding of the invention.

The invention relates to a process for preparing lignocellulosic material into
  a. a mixture of phenolic mono-, di- and polyphenolic compounds,
  b. a mixture of sugar-derived polyols and oligosaccharides,
  c. and a solid, cellulose-enriched material
by subjecting lignocellulosic material in particulate form to a treatment with a. a liquid medium comprising water and an alcohol solvent at a temperature of
at least 150° C.,
b. in the presence of a catalyst based on ruthenium or nickel.
c. externally supplied hydrogen gas.

Figure 3:
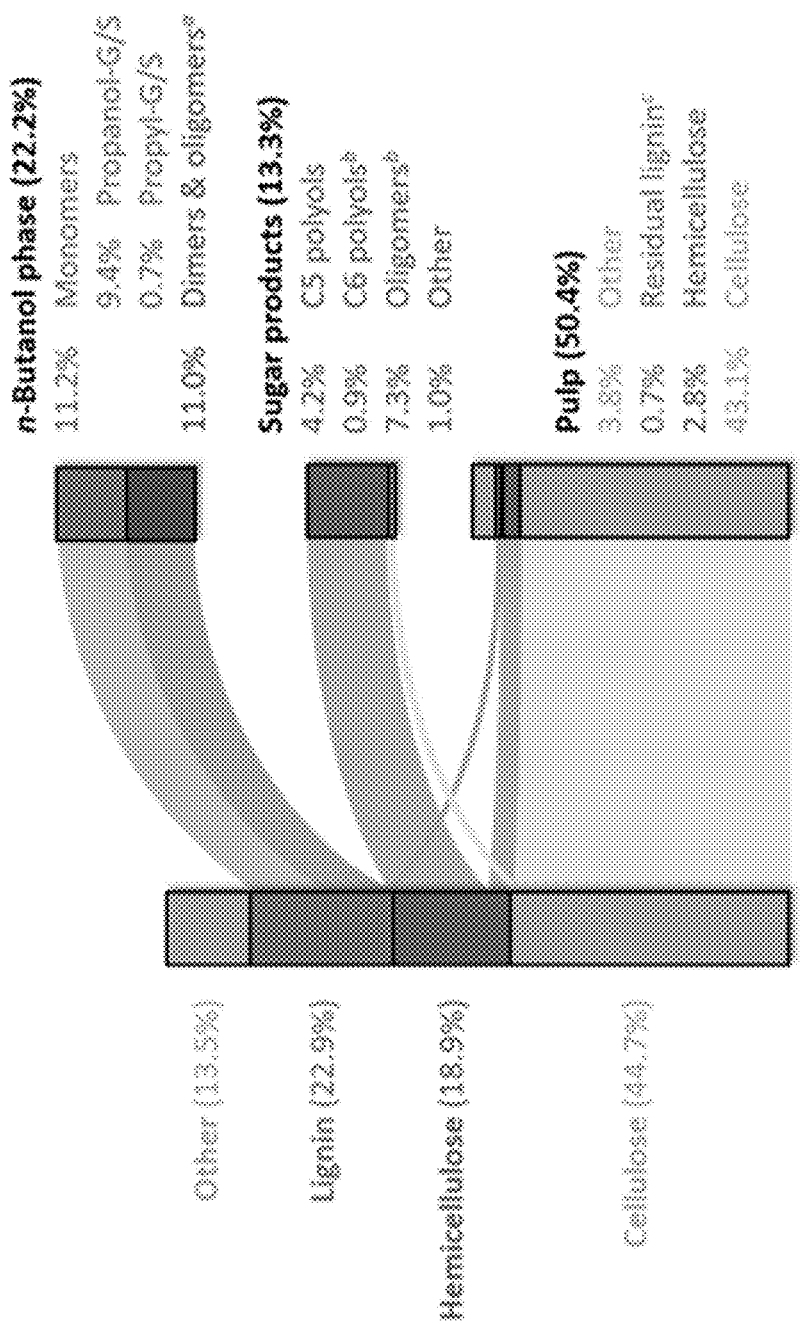
FIG. 3 provides an overview of the fractions obtained from RCF in n-butanol/water (right), in relation to the composition of the biomass (left). All numbers are expressed as wt% relative to the pre-extracted eucalyptus substrate. Reaction conditions: 20 mL water, 20 mL butanol, 0.2 g Ru/C, 2 g Eucalyptus sawdust, 200° C., 2 h, 30 bar $H_2$, [a]Based on: the n-butanol oil, apart from lignin monomers (FIG. 2A), solely consists of dimers and oligomers. [b]It could not be resolved to what extent C6 polyols and oligomers originate from cellulose. The high retention of cellulose in the pulp at least indicates that oligomers mainly originate from hemicellulose. [c]Based on the n-butanol oil yield.

Referring to FIG. 1, the disclosed catalytic process employs an organic-solvent mixture to extract lignin and hemicellulose from the starting lignocellulosic material, while leaving the cellulose as a solid. The extracted compounds are treated with a Ruthenium- or a Nickel-based catalyst under hydrogen atmosphere which produces phenolic monomers, dimers and oligomers; and polyols, including pentitols and hexitols. The mass balance is shown in FIG. 3.

The main highlights of this invention are (1) the use of intact, solid lignocellulosic material, (2) the process selectively extracts lignin and hemicellulose while leaving the cellulose as a solid, (3) the process yields three product streams, each derived from a main lignocellulosic material constituent, (4) the product streams can be easily isolated by means of filtration and liquid-liquid extraction, (5) the selectivity of the substitution pattern of the phenolic monomers, dimers, and oligomers can be controlled—a high selectivity towards 4-(3-hydroxy-propyl)-guaiacol and 4-(3-hydroxy-propyl)-syringol can be obtained (>60 wt % of the obtained monomers, such as >80 wt %). This third point underscores the power of the disclosed catalytic method to convert both lignin and hemicellulose using the same transition metal catalyst, yielding lignin-derived phenolics and hemicellulose-derived C5 and C6 polyols. The fifth point underscores the power of the disclosed method to selectively yield products (see for instance EXAMPLE 3 and 6). Phenolic product selectivity can be altered, which is believed to be a desirable feature. Lignocellulosic material suitable for the process according to the invention includes lignocellulosic biomass, such as hardwood, softwood, and herbaceous biomass, including grasses and straws. Biomass can be supplied in the form of forestry residues and products (e.g. trees), crops (e.g. energy crops such as grasses and short rotation coppice wood), agricultural residues (such as flax shives, sugar cane bagasse), yard waste, animal and human waste (such as biodegradable municipal waste, waste wood). Such biomass comprises in general 20 to 80 wt % carbohydrates (based on dry matter), which are valuable starting materials for production of chemicals in a biorefinery.

In one embodiment of the invention, biomass originating form genetically modified plants is used. In one particular embodiment, genetically modified poplar wood is used. Genetic modification is a tool to alter the biomass structure, such as the lignin structure. This may lead to easier lignin extraction, higher monomer yields, or other phenolic products, such as catechols and substituted catechols.

In one embodiment of the invention, the lignocellulosic material is pre-extracted with an organic solvent, a mixture of organic solvents, or a mixture of organic solvent(s) and water, at temperature below 125° C. For example a toluene-ethanol or a water-ethanol mixture is used. Typically a soxhlet apparatus is used for this optional pre-extraction. The pre-extraction cleans the lignocellulosic material, for example by removing extractives such as fatty acids or terpenes. The process according to the present invention can also be performed without pre-extracting the lignocellulosic material according to such a procedure.

In one embodiment of the invention, the alcohol solvent to be used according to the invention, is one alcohol solvent or a mixture of organic solvents comprising at least one alcohol solvent.

In one embodiment of the invention, lower alcohols and diols, are used as the alcohol solvent. Herein, "lower" means containing 1-6 carbon atoms ($C_1$-$C_6$). Examples of suitable lower alcohols include, but are not limited to, methanol, ethanol, 2-propanol, 2-methyl-propanol, ethylene glycol, glycerol, or a mixture thereof.

In one embodiment of the invention, the alcohol solvent to be used according to the invention is not fully miscible with water when below 100° C. Hence, in this embodiment, the liquid medium comprises a biphasic mixture (when below 100° C.). In one embodiment, suitable solvents are alcohol solvents such as n-butanol, 1-pentanol, 2-pentanol, 3-methylbutan-1-ol, 2-ethyl hexan-1-ol.

In one embodiment of the invention, the ratio between the alcohol solvent and water varies from 1:10 to 10:1 (alcohol:water volume ratio), such as 1:8 to 8:1, preferably 1:4 to 4:1, or 1:2 to 2:1, preferably around 1:1.

In one embodiment of the invention, the ratio between the alcohol solvent and water varies from 1:10 to 10:1 (alcohol:water volume ratio), such as 1:8 to 8:1, preferably 1:4 to 4:1, or 1:2 to 2:1, preferably around 1:1 The biomass is mixed with the liquid medium for a reaction time of 0.05-12 h, more preferably 0.5-6 h, such as 2 h. The temperature of the liquid medium is between 150° C. to 240° C., such as 170° C. to 220° C., preferably in the range of 180° C. to 210° C. The treatment time depends on the temperature, the solvent type, and the solvent-to-water ratio. A preferable combination is an equivolumetric mixture of n-butanol and water, a reaction temperature of 200° C., and a treatment time of 2 h. Higher treatment temperature requires a lower treatment time and/or lower solvent-to-water ratio, and vice versa.

Higher water-to-solvent ratio requires a lower treatment time and/or a lower treatment temperature, and vice versa. Higher treatment time requires a lower treatment temperature and/or a lower water-to-solvent ratio, and vice versa.

According to the invention, a catalyst based on ruthenium or nickel is used in the process to treat lignocellulosic biomass. In one embodiment, the Ru or Ni is used as a metal on a support. In a preferable embodiment, the catalyst is Ru/C. In another embodiment, the catalyst is Ni/C, Ni/$Al_2O_3$, Ni/$SiO_2$, Ni/$ZrO_2$, Ni/$SiO_2$—$Al_2O_3$, Ru/$Al_2O_3$, Ru/$SiO_2$, Ru/$ZrO_2$, Ru/$SiO_2$—$Al_2O_3$. The catalyst may be pre-activated prior to use for example by removal of oxygen or oxides through the use of a reducing agent. The catalyst may be added in at least catalytic amounts. In one embodiment of the invention, the catalyst-to-biomass ratio is in the range of 20-2 wt %, such as 10-5 wt %.

In another embodiment of the invention, the Ru or Ni is not used on a support. In one particular embodiment, RaneyNi is used as the catalyst.

The process of the present invention does involve the use of hydrogen gas. In one embodiment of the present invention, the partial pressure of hydrogen gas (herein referred to simply as "hydrogen pressure") exceeds atmospheric pressure. More preferably, the hydrogen pressure is in the range of 1-50 bar (at room temperature), such as 5-40 bar, 10-30 bar, or 15-25 bar.

In one embodiment of the present invention, the process is performed in a closed or sealed container, herein referred to as a batch reactor, creating an autogenous pressure. The reaction is preferably conducted with continuous mixing.

The pressure during the depolymerization may be around 100 bar or less, or 50 bar or less, or 45 bar or less, or 35 bar or less, or 25 bar or less.

In one embodiment, the process of the present invention is performed in a flow-through reactor, which is a vessel or tube wherein the liquid medium is continuously added and removed. During the treatment the solid lignocellulosic material remains in the reactor vessel or tube, whereas extracted lignin and hemicellulose are removed from the reactor as they are solubilised in the solvent. In one embodiment, the catalyst is present within the same tube or vessel. In another embodiment, the catalyst is present in a second vessel or tube (referred to as "second stage"). In this embodiment, the solvent containing extracted lignin and hemicellulose is added to the second stage when exiting the vessel or tube containing the biomass. Hydrogen gas needs to be added only to the second stage. In one embodiment, the process of the present invention is performed in a continuous reactor, which is a vessel or tube wherein the liquid medium and lignocellulosic material are continuously added and removed as a slurry. Extracted lignin and hemicellulose are removed from the reactor as they are solubilised in the solvent. In one embodiment, the catalyst is present within the same tube or vessel. The catalyst can be physically contained so that it remains in the tube, or it can be continuously added and removed as part of the slurry. Hydrogen gas needs to be added to the reaction vessel or tube. In another embodiment, the catalyst is present in a second vessel or tube, the solvent containing extracted lignin and hemicellulose is added to the second stage after exiting the vessel or tube containing the biomass. Hydrogen gas needs to be added only to the second stage. In one embodiment, the solid, cellulose-enriched pulp obtained from the process of the present invention is isolated from the liquid medium by means of filtration, centrifugation, or any suitable technique. The cellulose-content of the pulp is higher than the cellulose-content of the initial lignocellulosic material, therefore, the term "cellulose-enriched" is used. In one embodiment of the invention, the cellulose-content of the obtained pulp is higher than 50% by mass, for example 65%, or 80%, depending on the cellulose content of the used lignocellulosic material. The cellulose-enriched pulp can be used as a material additive, or can be treated with enzymes, producing for example ethanol or n-butanol.

In one embodiment, the mixture of phenolic mono-, di- and polyphenolic compounds is isolated from the mixture of sugar-derived polyols and oligosaccharides, by means of liquid-liquid extraction.

In one embodiment of the invention, the mixture of phenolic mono-, di- and polyphenolic compounds is isolated from the mixture of sugar-derived polyols and oligosaccharides by means of liquid-liquid extraction using water and an organic solvent. Phenolic mono-, di- and polyphenolic compounds are contained in the organic solvent-rich phase. Sugar-derived polyols and oligosaccharides are contained in the water-rich phase.

In one embodiment of the invention, said liquid medium comprising water and alcohol solvent is first removed, for example by evaporation, followed by liquid-liquid extraction using water and an organic solvent to isolate the mixture of phenolic mono-, di- and polyphenolic compounds from the mixture of sugar-derived polyols and oligosaccharides. Suitable organic solvents for performing said liquid-liquid extraction include, but are not limited to, dichloromethane, chloroform, ethylacetate, or n-butanol.

In one embodiment of the invention, said liquid medium comprising water and an alcohol solvent is used to isolate the mixture of phenolic mono-, di- and polyphenolic compounds from the mixture of sugar-derived polyols and oligosaccharides by means of liquid-liquid extraction. In one embodiment of the invention, this is achieved when the liquid medium is biphasic below 100° C., for example when the liquid medium is a mixture of n-butanol and water. In another embodiment of the invention, an additional compound is added to the liquid medium to induce phase separation and allow liquid-liquid extraction.

In one embodiment of the invention, the organic solvent used for liquid-liquid extraction is removed by evaporation, yielding an isolated mixture of phenolic compounds. The mixture of phenolic compounds or composition according to the present invention may be further separated into different subfractions, for example by distillation, membrane separation, liquid-liquid extraction, any other suitable technique, or a combination thereof. Isolated phenolic compounds may be used for preparing materials (such as resins, polymers), fine chemicals (such as pharmaceuticals, fragrances), or bulk chemicals (such as phenol, terephthalic acid).

In one embodiment of the invention, the obtained phenolic product mixture is an oil, and has average molecular weight of not more than 1500 $g \cdot mol^{-1}$, such as <1000 $g \cdot mol^{-1}$, for example <750 $g \cdot mol^{-1}$.

In one embodiment of the invention, the percentage by mass of said mono-, di-, and polyphenolic compounds relative to the total lignin content of said lignocellulosic material, is higher than 35%, for example 50%, 75%, or 85%.

In one embodiment of the invention, the percentage by mass of monophenolic compounds in said mixture of mono-, di- and polyphenolic compounds, is between 20% and 100%, such as between 35 and 70%, for example 50±5%.

In one embodiment of the invention, the yield of monophenolic compounds is between 12% and 60%, such as between 20 and 50%, for example from 30-40%; on mass basis relative to the lignin content of the used lignocellulosic material. The yield depends on the lignin structure, which is determined by the type of lignocellulosic material. In one embodiment of the invention, hardwood is used, such as birch wood, beech wood, *Eucalyptus* wood or poplar wood. 60-75% of inter-unit linkages of lignin residing in hardwood are cleavable ether linkages. Based on this number, a theoretical yield of monophenolic compounds is in the range of 36-56 wt % (calculated by squaring the percentage of cleavable bonds). In another embodiment of the invention, softwood is used as lignocellulosic material, such as pine wood or spruce wood. In softwood, 35-50% of inter-unit linkages are cleavable ether linkages, corresponding to a yield in the range of 12-25 wt %.

In one embodiment of the invention, more than 60% by mass of the monophenolic compounds in said mixture of mono, di- and polyphenolic compounds, comprises 4-(3-hydroxy-propyl)-guaiacol, 4-(3-hydroxy-propyl)-syringol. For example, >70% by mass of the monophenolic compounds comprises 4-(3-hydroxy-propyl)-guaiacol and 4-(3-hydroxy-propyl)-syringol. For example, >80% by mass of the monophenolic compounds comprises 4-(3-hydroxy-propyl)-guaiacol and 4-(3-hydroxy-propyl)-syringol. This feature is particular, because such a high selectivity (and high yield) with ruthenium- or nickel-based catalysts toward these compounds is unprecedented.

The high selectivity towards propanol-substituted compounds is also reflected in the lignin dimers an oligomers. As a results, the lignin oil—a combination of monomers, dimers, and oligomers—has a high content of aliphatic OH groups. A high aliphatic OH group content herein means more than 3 mmol aliphatic OH groups per gram lignin oil, such as 4 mmol or more aliphatic OH groups per gram lignin oil, as determined by P-NMR. This feature is particular, because such a high OH-group content with ruthenium- or nickel-based catalysts is unprecedented. For example, the use of ruthenium catalyst yields a lignin oil with low aliphatic OH group content. Low herein means lower than 2 mmol aliphatic OH groups per gram lignin oil, such as 1.5 mmol aliphatic OH groups per gram lignin oil.

In one embodiment of the invention, more than 60 wt %, such as 80 wt %, of the dimers according to the structure

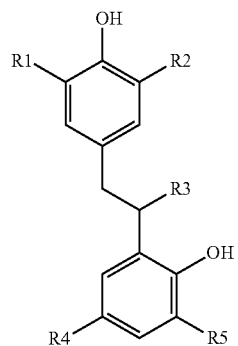

are dimers wherein R4 is —CH$_2$—CH$_2$—CH$_2$—OH.

In one embodiment of the invention, more than 60 wt %, such as 80 wt %, of the dimers according to the structure

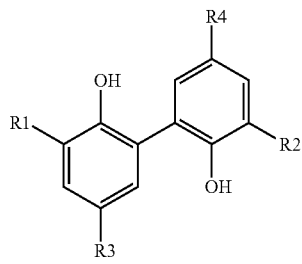

are dimers wherein each R3 and R4 is —CH$_2$—CH$_2$—CH$_2$—OH.

In one embodiment of the invention, the yield of 4-(3-hydroxy-propyl)-guaiacol, 4-(3-hydroxy-propyl)-syringol obtained by the process equals more than 15%, for example in the range of 25%-50%, such as 35% or 45% by mass relative to the lignin content of the used lignocellulosic material The G/S ratio of the phenolic monomers depends on the lignin structure, which is determined by the type of lignocellulosic material. In one embodiment of the invention, biomass is used wherein lignin mainly comprises guaiacols, such as softwood. In this embodiment of the invention, the obtained monophenolics are mainly guaiacols, such as 4-(3-hydroxy-propyl)-guaiacol, 4-n-propylguaiacol, and ethylguaiacol. In another embodiment of the invention, biomass is used wherein lignin comprises both guaiacols and syringols, such as hardwood. In this embodiment of the invention, the obtained phenolics are mainly guaiacols and syringols, such as 4-(3-hydroxy-propyl)-guaiacol, 4-(3-hydroxy-propyl)-syringol, 4-n-propylguaiacol, 4-n-propylsyringol, and ethylsyringol. In one embodiment of the invention, the aqueous solvent used for liquid-liquid extraction is removed, yielding an isolated mixture comprising polyols and oligosaccharides. Polyols can be used as low calorie sweeteners, or can be used for making fine chemicals. The molecular structure of the obtained polyols depends on the hemicellulose type, which is determined by the type of lignocellulosic material. In one embodiment of the invention, biomass is used wherein hemicellulose comprises mainly xylan, such as hardwood. In this embodiment of the invention, the obtained polyols are mainly xylitol. In another embodiment of the invention biomass is used wherein hemicellulose mainly comprises xylomannan, such as softwood. In this embodiment of the invention, the obtained polyols are mainly xylitol and mannitol.

In one embodiment of the invention, an additive is added to the liquid medium prior to the treatment of the lignocellulosic material. An additive can enhance the rate and extent of extraction and depolymerisation of lignin and hemicellulose.

In one embodiment of the invention, an acidic additive is added to the liquid medium prior to the treatment, which can enhance the rate and extent of extraction and depolymerisation of lignin and hemicellulose. The concentration of the acid catalyst in the solvent system can be in the range of 0.1 mM and 25 mM. Acidic additives are suitable to adjust the ratio of oligosaccharides to polyols.

In one embodiment of the invention, a mineral acid is added to the liquid medium prior to the treatment. Example of suitable mineral acids include, but are not limited to, hydrochloric acid, sulphuric acid and phosphoric acid.

In another embodiment of the invention, a carboxylic acid is added to the liquid medium prior to the treatment. Example of suitable carboxylic acids include, but are not limited to, acetic acid, formic acid, and mixtures thereof. In one embodiment, acetic acid originates from deacetylation of hemicellulose present in lignocellulosic material.

In another embodiment of the invention Lewis acid catalyst is added to the liquid medium prior to the treatment. Example of suitable Lewis acids include, but are not limited to AlCl$_3$, ZnCl$_2$, FeCl$_3$, Ni(II)-triflate, Cu(II)-triflate, Al(III)-triflate, Yb(III)-triflate, Sc(III)-triflate, La(III)-triflate, Hf(IV)-triflate.

In one embodiment of the invention, the used catalyst powder is isolated from the solid cellulose-enriched pulp by washing the obtained solid residue with a biphasic solvent medium, such as n-butanol/water. In one embodiment of the invention, the catalyst powder is a carbon-supported catalyst, Ru/C or Ni/C. Carbon-supported catalyst is relatively apolar and primarily resides in the organic phase, such as n-butanol. The pulp on the other more polar, and is located in the aqueous phase. After liquid-liquid extraction, the n-butanol phase containing part of the Ru/C was removed and fresh n-butanol was added to start another washing cycle.

Examples

Example 1

20 mL n-butanol, 20 mL water, and 0.2 g of Ru/C catalyst powder were added to a 100 mL batch reactor, together with 2 g of pre-extracted *Eucalyptus* sawdust. A general scheme of the process is presented in FIG. 1. The composition of the *Eucalyptus* substrate is summarised in Table 1.

TABLE 1

Compositional analysis of pre-extracted eucalyptus sawdust.

| Constituent | Content/wt % |
|---|---|
| Glucan (cellulose) | 44.66 |
| Hemicellulose | 18.92 |
| C5 carbohydrates | 16.37 |
| Xylan | 15.98 |
| Arabinan | 0.39 |
| C6 carbohydrates | 2.56 |
| Mannen | 1.13 |
| Galactan | 1.43 |
| Lignin | 22.90 |
| Acid insoluble | 21.45 |
| Acid soluble | 1.45 |
| Acetate | 3.70 |
| Water[b] | 4.12 |
| Total | 94.30 |

[b]Water content was measured gravimetrically by drying overnight at 120° C.

The reactor was sealed, purged with nitrogen, and pressurised with hydrogen (30 bar at room temperature), stirred (750 rpm), and heated to a reaction temperature of 200° C. for 2 h. After cooling, the reactor contents were quantitatively collected and filtered. The residual solids (pulp and catalyst) were washed with additional water (+100 mL) and n-butanol (+33 mL). Next, the pulp was dried in an oven at 80° C. The resulting pulp yielded 50.4 wt % of the initial biomass and retained most of the cellulose (96 wt % retention), whereas the major part of the hemicellulose was removed (85 wt % solubilisation). The filtrate instantly separated into an organic and aqueous phase (FIG. 1), containing depolymerised lignin and hemicellulose, respectively, thereby providing a facile and effective separation of the solubilised products. Additional extraction of the aqueous phase with butanol was performed twice (2×33 mL). Evaporation of n-butanol (120 mL total) yielded a viscous oil, which after drying measured 22.2 wt % of the initial biomass weight and 97 wt % relative to the initial lignin content. The weight of the n-butanol lignin oil is close to the total lignin content of the *Eucalyptus* sawdust (22.9 wt %), indicating extensive lignin extraction from the biomass. The obtained lignin oil (from the n-butanol phase) is rich in phenolic monomers, corresponding to a yield of 48.8 wt %, as measured by GC-FID and based on total lignin content of the pre-extracted *Eucalyptus* sawdust (Table 1). 85 wt % of the monomer products comprise propanol-substituted syringol (S) and guaiacol (G), with a smaller fraction consisting of propyl- and ethyl-substituted analogues (FIG. 2A). Noticeably, previous work on Ru/C-catalysed RCF reported the selective formation of propyl-G/S when processing sawdust in pure methanol at 250° C. (Van den Bosch et al., *Energy Environ. Sci.*, 2015, 8, 1748-1763). The use of Ru/C in aqueous medium surprisingly yields valuable propanol-substituted phenolics in close-to-theoretical yields.

Figure 13:
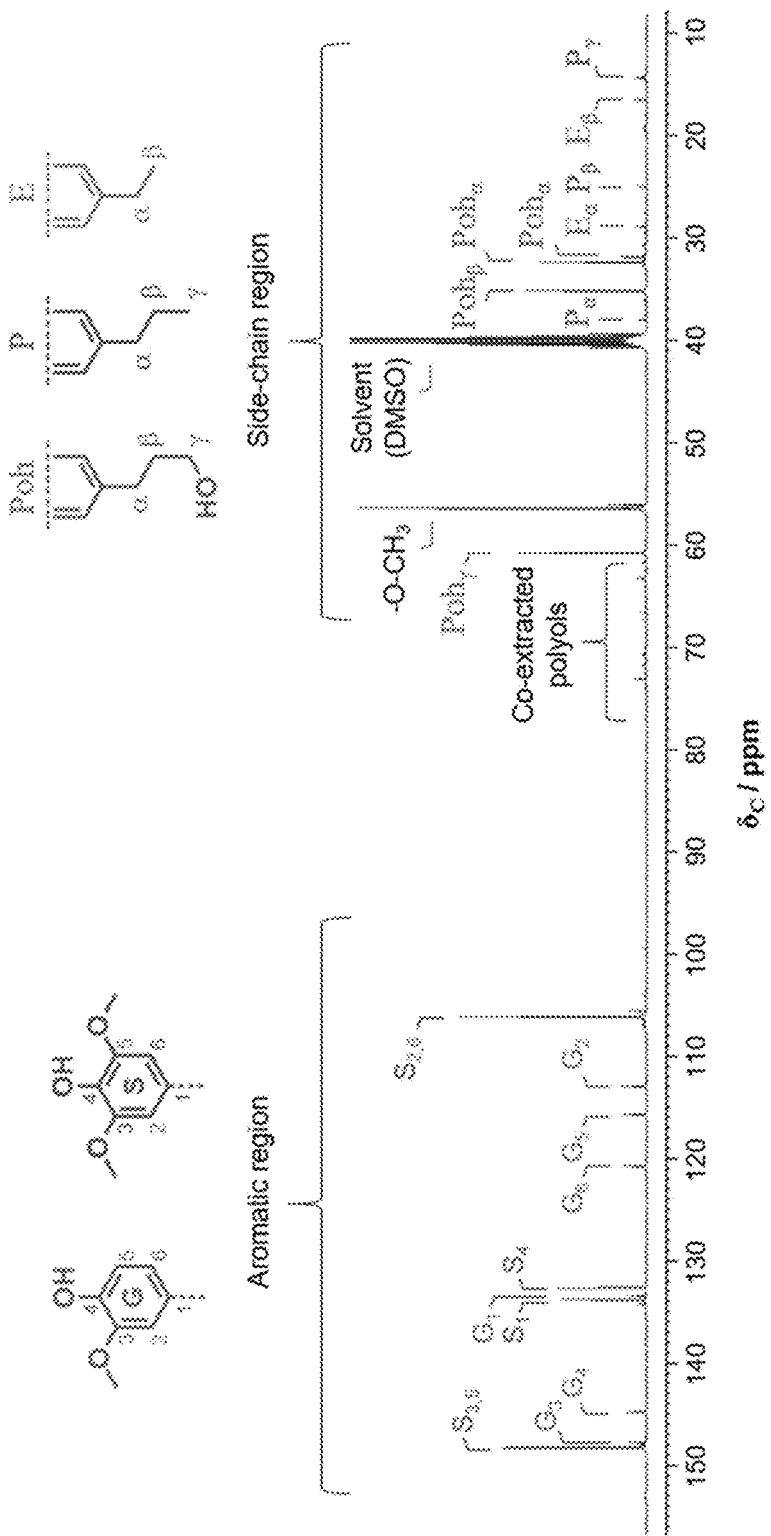
FIG. 13 is a $^{13}$C NMR of lignin oil (n-butanol phase) from Ru/C-catalysed RCF (as described in EXAMPLE 1), with assignment of signals. Reaction conditions: 20 mL n-butanol, 20 mL water, 2 g pre-extracted eucalyptus sawdust, 0.2 g Ru/C, 30 bar H$_2$ at room temperature, 200° C., 2 h.

The molecular weight distribution of the lignin-derived products in the n-butanol phase was assessed by gel permeation chromatography (GPC). The GPC chromatogram depicted in FIG. 2C shows that the organic phase contains monomers, dimers, trimers, and small oligomers. The largest oligomers elute at 7 min, which corresponds to a MW of 1850 g mol$^{-1}$ (DP of circa 10); with average M. of the oil being below 1500 g mol$^{-1}$. Additionally, GPC corroborates the prevalence of propanol-substituted monomers, in alignment with GC-FID analysis. HSQC NMR (FIG. 2D) and $^{13}$C NMR (FIG. 13) support the identification of the obtained products, and furthermore evidence the almost complete absence of residual inter-unit ether bonds. Hence, we conclude that lignin undergoes effective and selective depolymerisation in the proposed alcohol/water RCF system.

Figure 5:
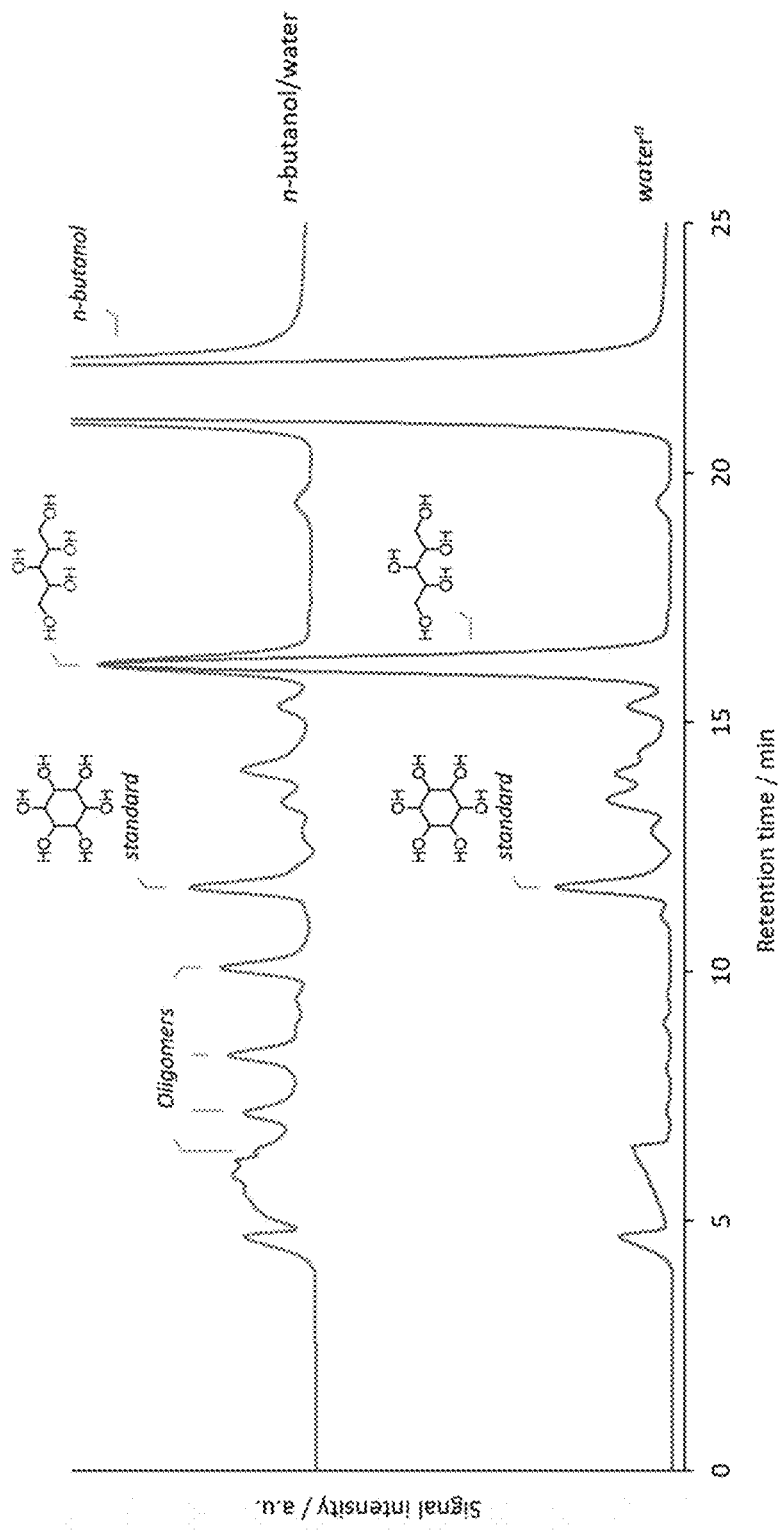
FIG. 5 is an HPLC chromatogram of the aqueous phases obtained from performing the process with (top) a butanol/water mixture and (bottom) pure water: in support of FIGS. 7A and 7B. Reaction scheme see FIG. 1. Reaction conditions: 40 mL liquid mediun, 0.2 g Ru/C, 2 g Eucalyptus sawdust, 200° C., 2 h, 30 bar $H_2$. After reaction, an extraction procedure was executed so that each reaction resulted in a an n-butanol phase and an ago ous phase (120 mL each).

The products in the aqueous phase were analysed by GC-FID following trimethylsilylation to increase volatility. Products detected by GC-FID mainly include C5 polyols (48 mg·g$_{biomass}^{-1}$), C6 polyols (10 mg·g$_{biomass}^{-1}$), and smaller quantities of non-reduced C5/C6 sugars, glycerol, propane diol, and ethylene glycol (FIG. 2B). In addition, HPLC was performed to identify non-volatile products present in the aqueous phase (FIG. 5). Signals corresponding to oligomers were observed, equaling 73 mg·g$_{biomass}^{-1}$. The combined yield of C5 polyols, C5 sugars, and oligomers is equivalent to ca 74% of the initial biomass C5 content (mainly xylan, Table 1). A general overview of the mass balance is presented in FIG. 3.

Example 2

To demonstrate the scalability potential of the process, an experiment was performed using a 2 L Parr batch reactor (i.e. a 20-fold increase of the reactor volume compared to EXAMPLE 1). The reactor was loaded with 80 g *Eucalyptus* sawdust (×40 compared to EXAMPLE 1), 8 g Ru/C (×40), 400 mL n-butanol and 400 mL water (×20). Note that the biomass-to-solvent ratio is two times higher compared to the ration in EXAMPLE 1, which is more desirable for industrial operation. The obtained pulp equals 50.9 wt % of the initial biomass, being quasi-similar to the pulp yield of the small scale reference (50.4 wt %). A high lignin monomer yield was achieved (43.7 wt %) with a 79 wt % selectivity towards propanol-substituted compounds. The yield of C5 polyols (67 mg·mL$^{-1}$) on the other hand is higher than the small scale reference experiment (48 mg·mL$^{-1}$). This discrepancy is ascribed to the higher biomass-to-solvent ratio, as was also observed on small scale. A higher biomass-to-solvent ratio leads to a slightly lower pH due to deacetylation of hemicellulose. Mildly acidic media facilitate the conversion of hemicellulose to C5 and C6 polyols (vide infra, EXAMPLE 9).

Example 3

Figure 12:
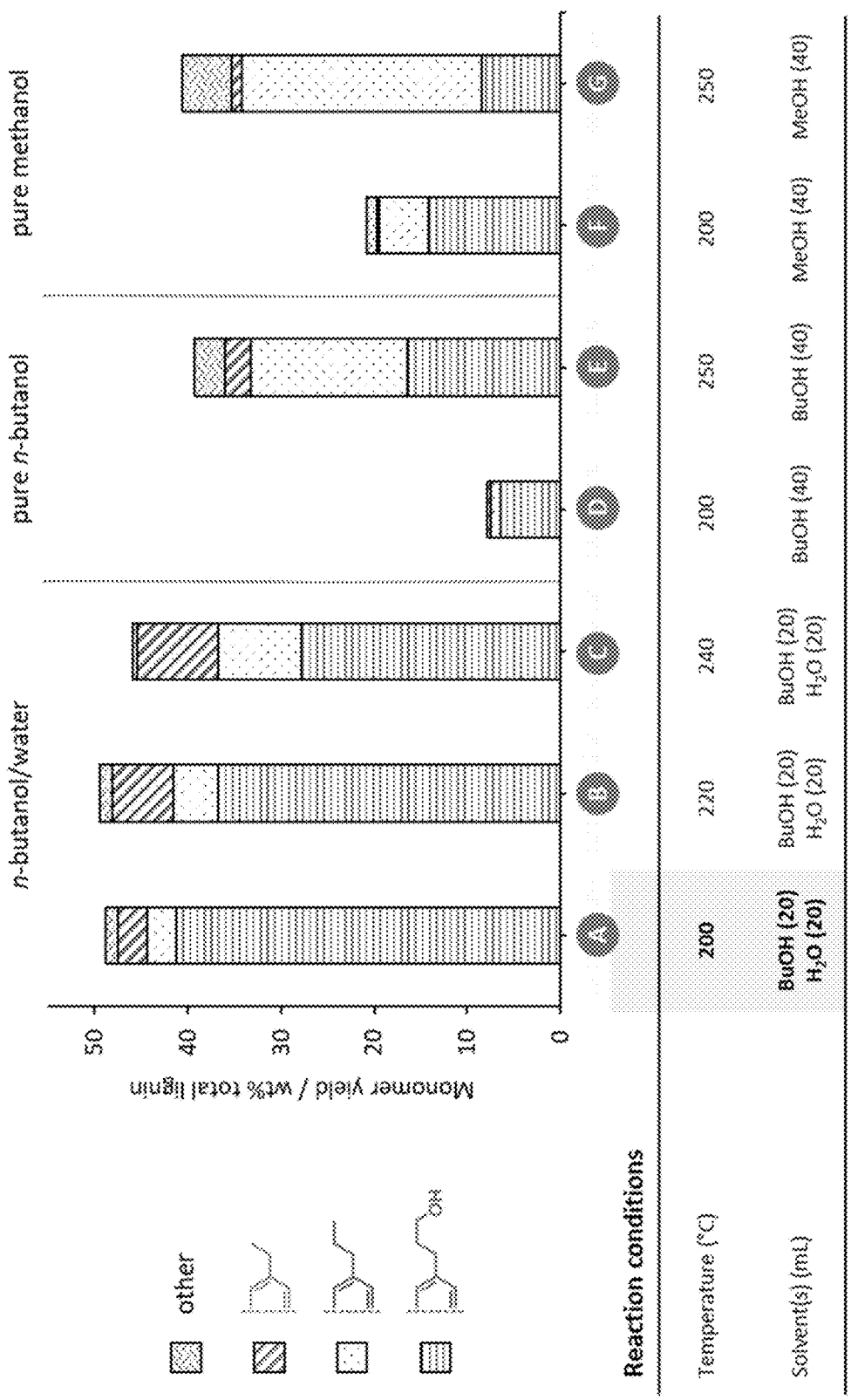
FIG. 12 shows Lignin monomer yield and distribution obtained from Ru/C-catalysed RCF of eucalyptus using different combinations of temperature and solvent, exemplifying the need for both alcohol and water to obtain both a high yield and selectivity towatds propanol-substituted phenolic products. Reaction conditions: 40 mL solvent, 200 ° C., 2 h, 30 bar H2 at room temperature, 2 g pre-extracted eucalyptus sawdust, 0.2 g Ru/C. Entry A corresponds to EXAMPLE 1.

In EXAMPLE 1, it was already mentioned that the total monomer yield approximates the theoretical maximum (48.8 wt % obtained monomer yield), and that 80%-90% by mass of the monophenolic compounds comprises 4-(3-hydroxy-propyl)-guaiacol and 4-(3-hydroxy-propyl)-syringol. The combination of this high total monomer yield and 4-(3-hydroxy-propyl) selectivity is unusual for using a Ru/C catalyst. To demonstrate this, the process as described in EXAMPLE 1 was performed under varying conditions, meaning with different solvents and at different reaction temperature. Results are summarised in FIG. 12. The process was for instance performed with pure BuOH (FIG. 12, bar D) and pure MeOH (FIG. 12, bar F) at 200° C. The total yield of monophenolic compounds is below 25 wt % relative to the initial lignin, although the selectivity towards propanol-substituted compounds is above 60 wt %. Increasing the temperature increases the total monomer yield, close to the theoretical maximum, though the selectivity towards propanol-substituted monomers decreases below 60 wt % of the detected monomers (FIG. 12, bars E and G). The most abundant type of phenolic monomers are propyl-G/S. Hence, a trade-off exists between high total monomer yield and high selectivity towards propanol-substituted phenolics. In addition, when using pure alcohol solvents, no hemicellulose-derived polyols are obtained because no hydrolysis occurs (FIG. 7, see also EXAMPLE 7).

The present invention (FIG. 12, bar A, that is EXAMPLE 1) fulfils the need of a process that is able to obtain high yields and selectivity towards propanol-substituted phenolics—breaking the earlier mentioned trade-off (FIG. 12, bars D-G)—while at the same time yielding hemicellulose-derived polyols. FIG. 12, bar A demonstrates the desirable effect of using a solvent/water mixture (in this example butanol/water) which are supportive to fulfil this need. First of all, since water is part of the mixture, hemicellulose is extracted and hydrolysed, yielding polyols (FIG. 2)—in contrast to using pure alcohol solvents. Polyols are formed by hydrolysis and hydrogenation of carbohydrate polymers. Water demonstrated to support the hydrolysis reaction and the catalyst (in this case Ru/C) was demonstrated to support hydrogenation reaction (see also EXAMPLE 5). Furthermore, the use of a butanol/water mixture enables to obtain high lignin monomer yields, with high selectivity towards propanol-substituted monomers. This leads to a high yield of propanol-substituted-G/S: 41.2 wt % relative to the initial lignin for the process as described in EXAMPLE 1. Even when the temperature is increased (FIG. 12, bars B and C) to 220° C. and 240° C., a high selectivity is obtained towards propanol-substituted monomers, which remains higher than 60 wt %. In contrast to FIG. 12, bars E and H, even at temperatures >200° C., propyl-substituted compounds are thus not the main phenolic products when using BuOH/water mixtures as solvent.

Counter Example 4

Figure 4A:
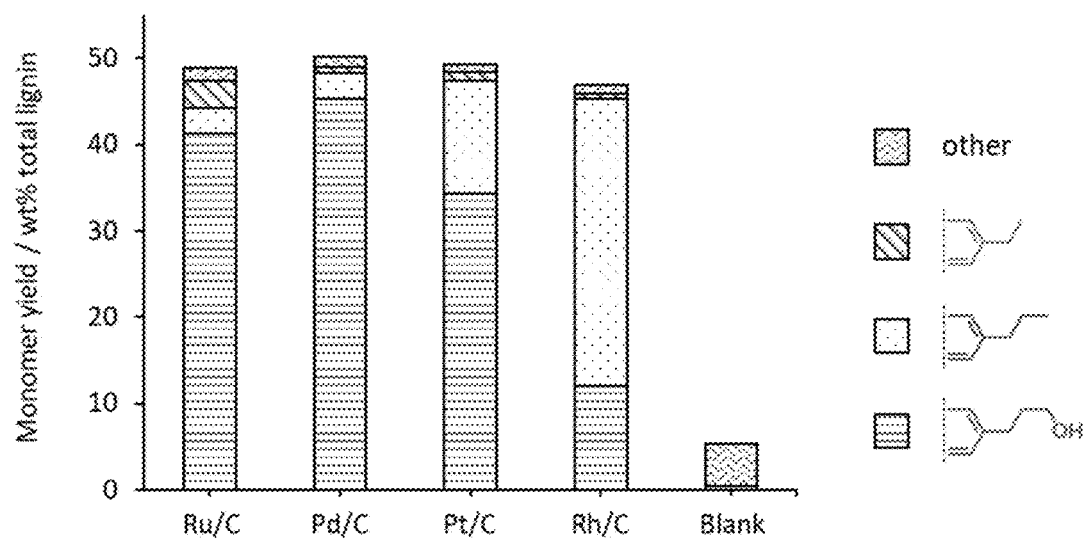
FIGS. 4A and 4B demonstrate Ligin monomers (FIG. 4A) and carbohydrate products (FIG. 4B) obtained from RCF in n-butanol/water with different catalysts. Reaction scheme see FIG. 1. Reaction conditions: 20 mL water, 20 mL butanol, 0.2 g catalyst, 2 g Eucalyptus sawdust, 200° C. 2 h, 30 bar $H_2$.
Figure 4B:
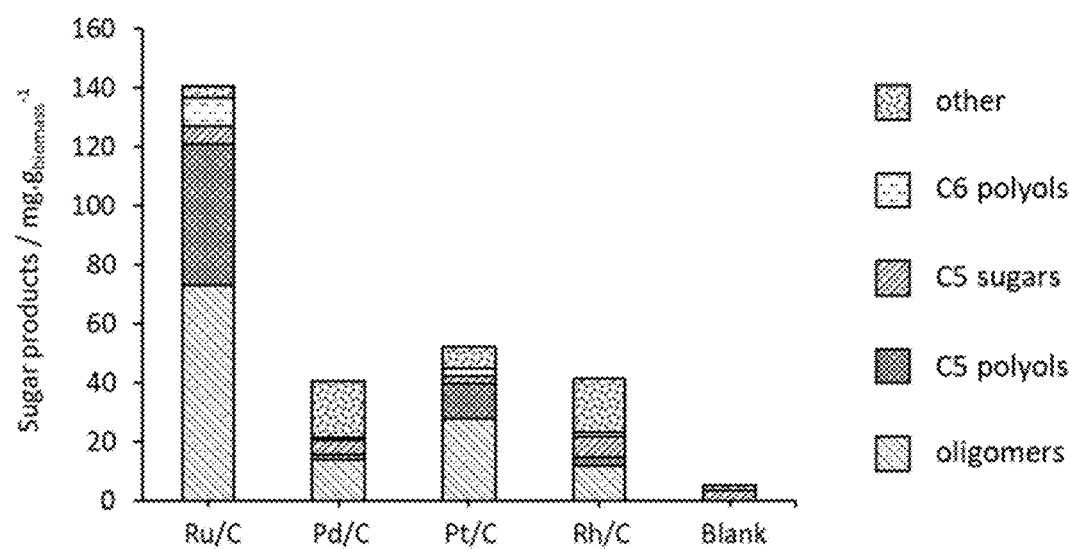

To illustrate the importance of the Ru/C catalyst, the process was performed with other noble metal catalysts. Pd/C, Pt/C, and Rh/C catalyst powders (5 wt % metal loading) were tested under the same conditions as described in EXAMPLE 1. All catalysts afford total lignin monomer yields in the range of 47-50 wt % based on total lignin content (FIG. 4A). Noticeably, the monomer selectivity differs strongly, with the ratio of propanol-substituted monomers to propyl-substituted monomers decreasing in the order of Pd≈Ru>Pt>>Rh. Panel B of FIG. 4 summarises the composition of the aqueous fraction for the different noble metal catalysts. RCF with Ru/C yields the highest amounts of C5 polyols, equaling 48 mg·$g_{biomass}^{-1}$ (Y=25 C %) as analysed by GC-FID. The C5 polyol yield for Pt/C is 12 mg·$g_{biomass}^{-1}$. For Pd/C and Rh/C, almost no C5 nor C6 polyols were detected, as was also verified by HPLC analysis. The yield of carbohydrate oligomers follows a similar trend, suggesting that these are reduced oligomers. Overall, the studied carbon-supported catalysts perform equally well in terms of total lignin monomer yield, but Pd/C and Rh/C are not able to yield hemicellulose derived polyols, as also shown in ACS Sustainable Chem. Eng., 2016, 4, 6894-6904 (Renders et al.). Ru/C combines a high total monomer yield with high selectivity towards propanol-substituted compounds, and highest yield of C5 polyols compared to the other tested catalysts.

Counter Example 5

A control run without catalyst and pressurised hydrogen (referred to as "blank") was executed as described in EXAMPLE 1. The lignin monomer yield only reached 5 wt % (FIG. 4A). GPC shows that the dark and very viscous oil obtained upon evaporation of n-butanol mainly comprises large phenolic oligomers, resulting from repolymerisation. No significant quantities of C5 polyols, sugars, or oligomers were detected in the aqueous phase. The results of the blank run justify the implementation of a reductive catalytic system, which is needed to hydrogenate reactive intermediates (unsaturated phenolic intermediates and sugars) into stable products (i.e. saturated phenolics and polyols). Without hydrogenation, the products specified according to the invention (see EXAMPLE 1) are not obtained Counter Example 6

Figure 6A:
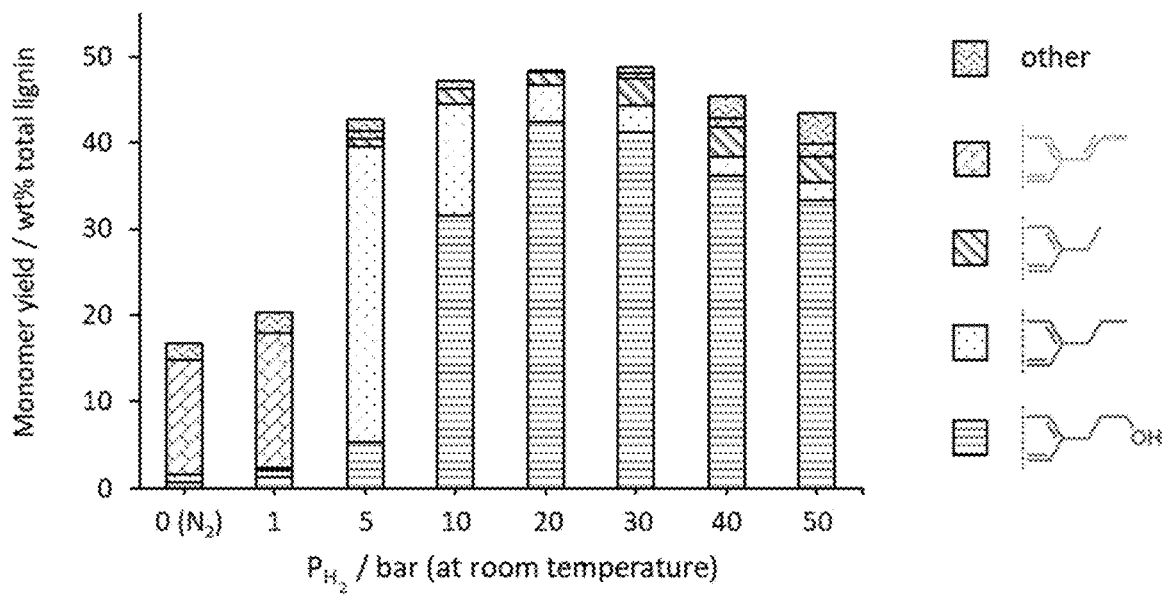
FIGS. 6A an 6B show Lignin monomers (FIG. 6A) and aqueous carbohydrate products (FIG. 6B) obtained fon RCF in n-butanol water with Ru/C and hydrogen pressure, Reaction scheme and reaction conditions: see FIG. 1. Reaction conditions: 20 mL water, 20 mL butanol, 0.2 g Ru/C, 2 g Eucalyptus sawdust, 200 ° C., 2 h. Reaction in absence of $H_2$ was performed under 30 bar $N_2$.

To show the impact of hydrogen pressure, the process as described in EXAMPLE 1 was performed under different hydrogen pressures, between 0 and 50 bar $H_2$. Without external hydrogen (30 bar $N_2$), the Ru/C-catalysed RCF process selectively yields propenyl-substituted monomers (FIG. 6A). The total monomer yield is low (17 wt %), because of inefficient stabilisation of reactive intermediates. Increasing the $H_2$ pressure to 5 and 10 bar strongly enhances the monomer yield, as well as the selectivity to propanol-substituted phenolics. The highest yields are obtained when 10-30 bar $H_2$ is applied.

Figure 6B:
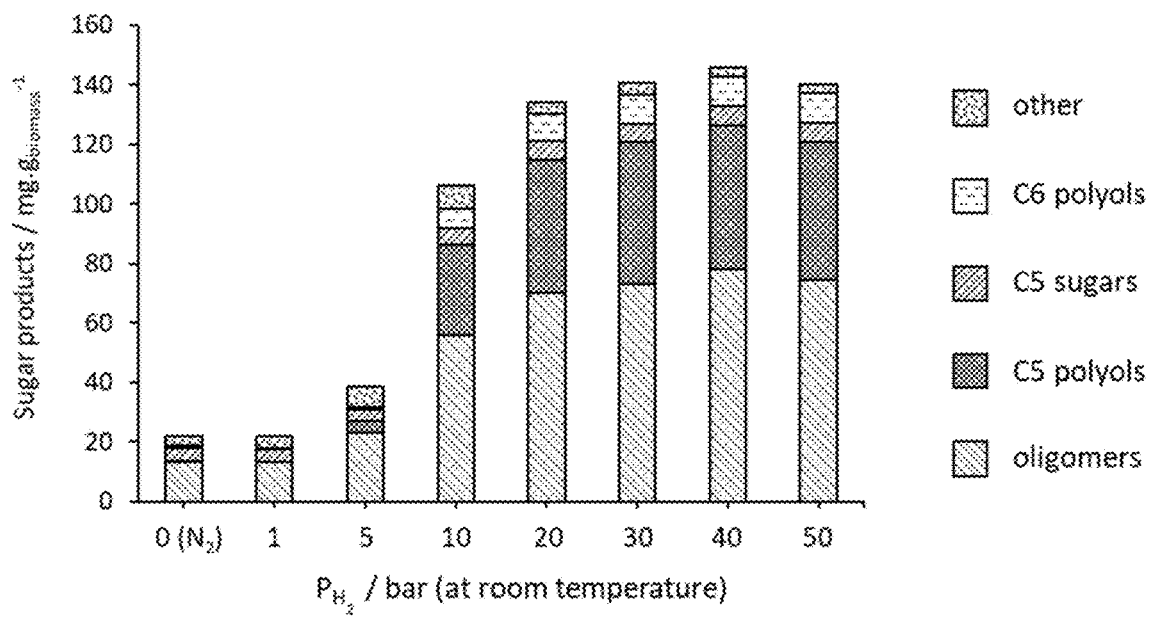

Under these conditions, propanol-substituted G/S are the predominant monomers. The requirement for hydrogen gas on the carbohydrate products in the aqueous phase is illustrated in FIG. 6B. In absence of pressurized hydrogen, the yield of targeted carbohydrate products is very low, which is ascribed to degradation (as indicated by the yellowish colour of the aqueous phase). With increasing pressure, the yield of C5 polyols gradually increases. The yield of carbohydrate oligomers follows a similar trend.

Counter Example 7

Figure 7A:
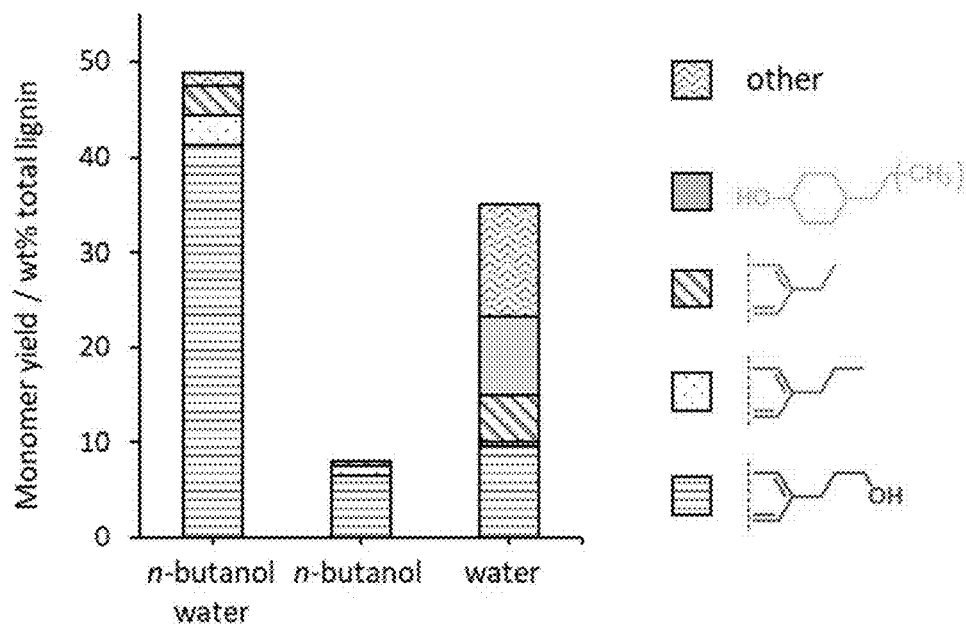
FIGS. 7A and 7B demonstrate the influence of RCF solvent composition on (FIG.7A) obtained lignin monomers and (FIG. 7B) aqueous carbohydrate products. Reaction scheme see see FIG. 1. Reaction conditions: 40 mL solvent, 0.2 g Ru/C, 2 g Eucalyptus sawdust, 200° C., 2 h, 30 bar $H_2$. After reaction, an extraction procedure was executed so that each reaction resulted in an n-butanol phase and an aqueous phase (120 mL each).
Figure 7B:
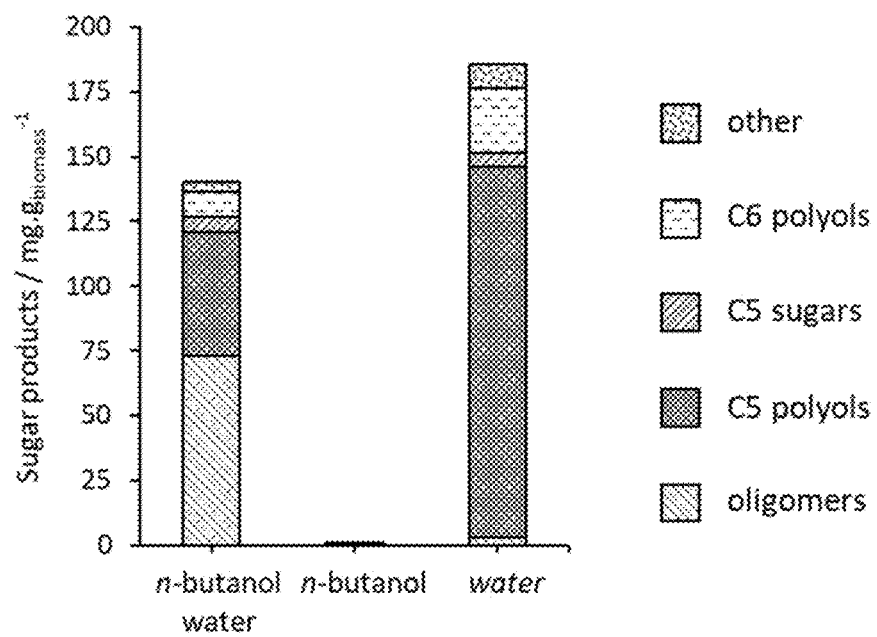

To illustrate the requirement of both water and organic solvent, the process as described in EXAMPLE 1 was performed in pure n-butanol (40 mL) as well as in pure water (40 mL). After reaction, a similar liquid-liquid extraction work-up procedure was performed to isolate sugar-derived products and lignin-derived products. When performing RCF in pure n-butanol, the biomass conversion and lignin oil yield measured 10.1 wt % and 5.6 wt % respectively, in contrast to 49.6 wt % and 22.2 wt % for the mixed solvent system. Hence, pure n-butanol is not effective for the intended RCF process, which is also reflected by the low lignin monomer yield (7.9 wt % on lignin basis, FIG. 7A) and insignificant amounts of carbohydrate products in the aqueous phase (FIG. 7B). Performing the RCF process in pure water affords a phenolic monomer yield (35.0 wt %) and oil yield (13.6 wt % of initial biomass) compared to processing in pure n-butanol. Total lignin monomer yields are lower compared to the mixed solvent system. More strikingly is the fact that lignin depolymerisation in pure water is less selective, with a significant fraction of the monomers comprising propylcyclohexanol and ethyl-cylohexanol (FIG. 7A). Ring hydrogenation of phenol proceeds faster in water than in mixed solvent system. Less than 60 wt % of the obtained monomer products are propanol-substituted G/S. The utilisation of an alcohol solvent thus protects the phenolic monomers from undergoing ring hydrogenation and subsequent demethoxylation. Hence, the mixed solvent system is required to obtain a high yield and high selectivity towards propanol-substituted monomers.

The yield of C5 polyols is circa threefold higher for the reaction in water compared to the mixed solvent system. This observation is ascribed to the higher polarity of pure water, which facilitates hemicellulose hydrolysis, as evidenced by the near absence of oligomers (FIG. 5). The high C5 polyol yield is thus compensated by a lower oligomer yield. Overall, a mixture of n-butanol/water affords higher lignin oil and total monomer yields compared to either pure n-butanol or pure water.

Example 8

The implementation of a Ni-based catalyst is shown. The process as described in EXAMPLE 1 was performed with Ni supported on silica/alumina (64 wt % metal loading). The total yield of monophenolic compounds equals 37.0% on mass basis relative to the lignin content of the starting lignocellulosic material. 92.5% by mass of the phenolic compounds comprises 4-(3-hydroxy-propyl)-guaiacol and 4-(3-hydroxy-propyl)-syringol. In contrast, the use of a similar Ni-based catalyst in pure methanol shows different selectivity: only 66% by mass of the monophenolic products comprise 4-(3-hydroxy-propyl)-guaiacol, 4-(3-hydroxy-propyl)-syringol, as reported by Van den Bosch et al. (Green Chem., 2017, 19, 3313-3326). The C5 polyol yield equals 42.6 mg per g biomass. The yield of oligosaccharides equals 32.5 mg per g biomass.

Example 9

The implementation of an acid additive is shown. The process as described in EXAMPLE 1 was performed with different amounts of HCl, in the range of 25-100 µmol (in 40 mL solvent mixture). The addition of HCl leads to an increased solubilisation of hemicellulose, from 85 wt % up to 94 wt %, while the cellulose fraction remains effectively retained in the pulp (~90 wt %). The yield of C5 polyols gradually increases with increasing acidity (FIG. 8B), from 48 g·gbiomass-1 (Y=25 C %) under neutral conditions to 113 mg·gbiomass-1 (Y=60 C %) when adding 100 µmol HCl. The addition of HCl enhance the conversion of hemicellulose. The total lignin monomer yield remains similar (in the range of 46.1-49.0 wt %).

Subsequently, we investigated if it is possible to perform the RCF process at lower temperature by adding higher amounts of HCl, since it is known that acidic additives promote both hemicellulose hydrolysis and delignification during RCF.39,40,54,90 Similar experiments were therefore conducted at 180° C. (0-200 µmol HCl) and 160° C. (0-400 µmol HCl). Results of this investigation are summarised in FIGS. 8A, 8B, 9A, and 9B. In neutral conditions, the n-butanol oil yield and lignin monomer yield decrease with decreasing temperature, pointing out incomplete delignification below 200° C.

Figure 8A:
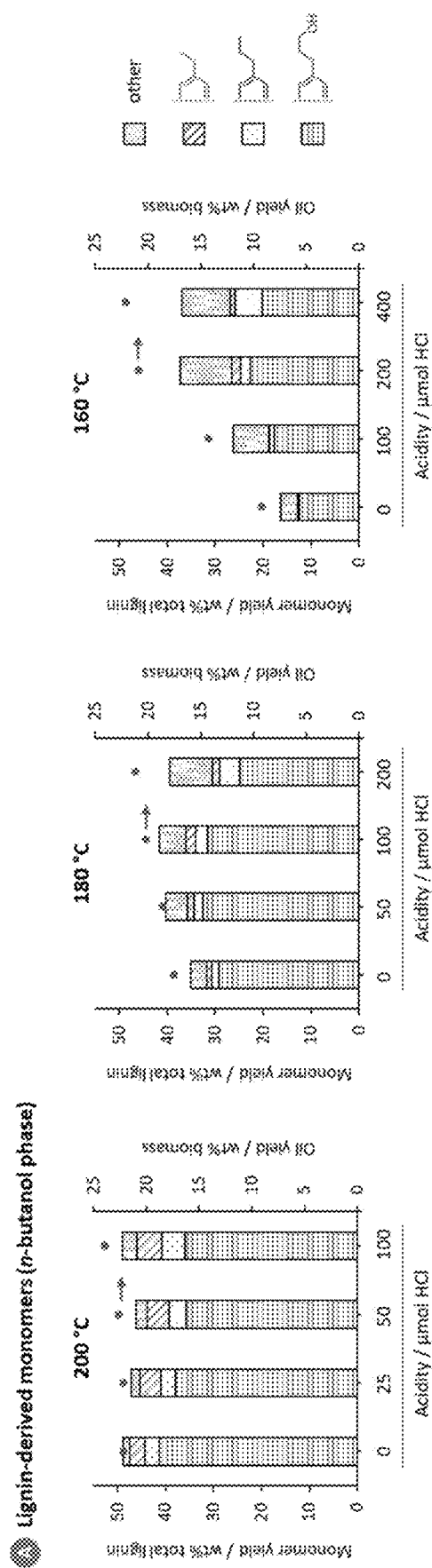
FIGS. 8A and 8B show a summary of the implementing of HC1 in n-butanol/water RCF.

The n-butanol oil yield was increased by adding HCl, thus showing that extensive biomass delignification can even be achieved at 160° C. (FIG. 8A). At temperatures below 200° C., also the lignin monomer yield increases with increasing acidity, but remains well below 48.8 wt %, which is the yield obtained under standard conditions (200° C., neutral). Acid-catalysed condensation may become more significant at high acid loadings, thereby reducing the total monomer yield. Moreover, high acid loadings (≥200 µmol HCl) negatively affect the selectivity towards propanol-G/S due to acid-catalysed side reactions. For instance, the fraction of propyl-substituted compounds increases, which is ascribed to acid-catalysed dehydration of the γ-OH group followed by hydrogenation. Another side reaction is the acid-catalysed etherification of the γ-OH group with n-butanol, leading to the formation of etherified monomers, the highest yield (3.7 wt %) of which was obtained at 160° C. with 400 µmol HCl. Nevertheless, propanol-substituted monomer are the most predominant monomer type. Overall, lignin disassembly is most effective and most selective under high temperature—low acidity conditions than under low temperature—high acidity conditions. This observation was also verified by GPC analysis. The chromatogram of the oil obtained at 160° C. (400 µmol HCl) displays relatively more oligomers and a smaller propanol-G/S signal compared to the oil obtained at 200° C. (100 µmol HCl). Yet, the main advantage of using acid additives, is the lower reaction temperature, which is favourable in terms of total pressure and energy input. This advantage might offset the lower phenolic monomer yield and selectivity.

Figure 8B:
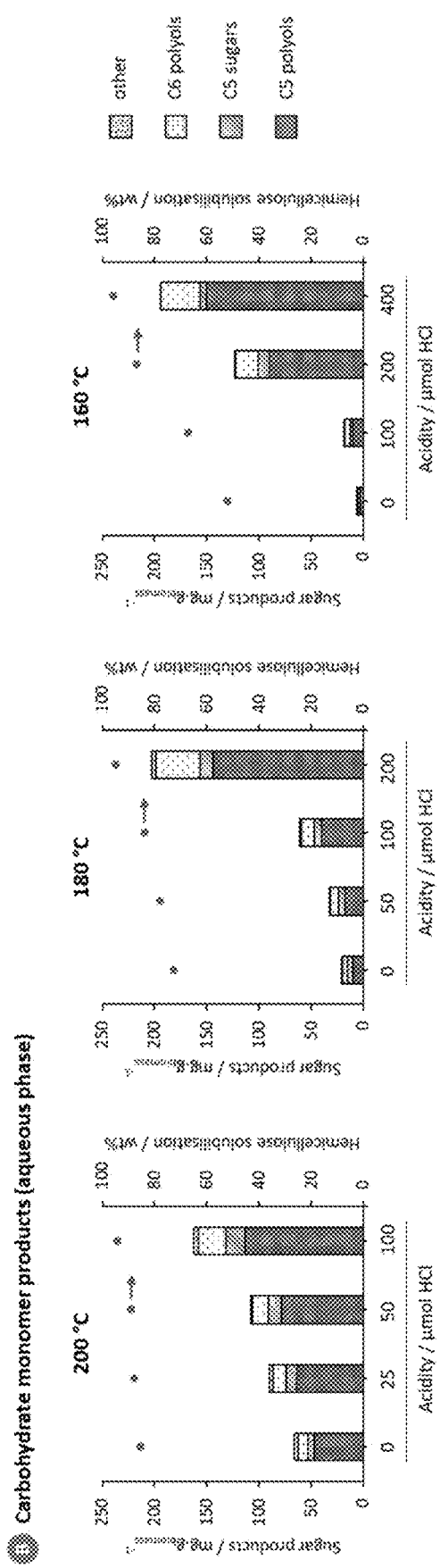
Figure 9A:
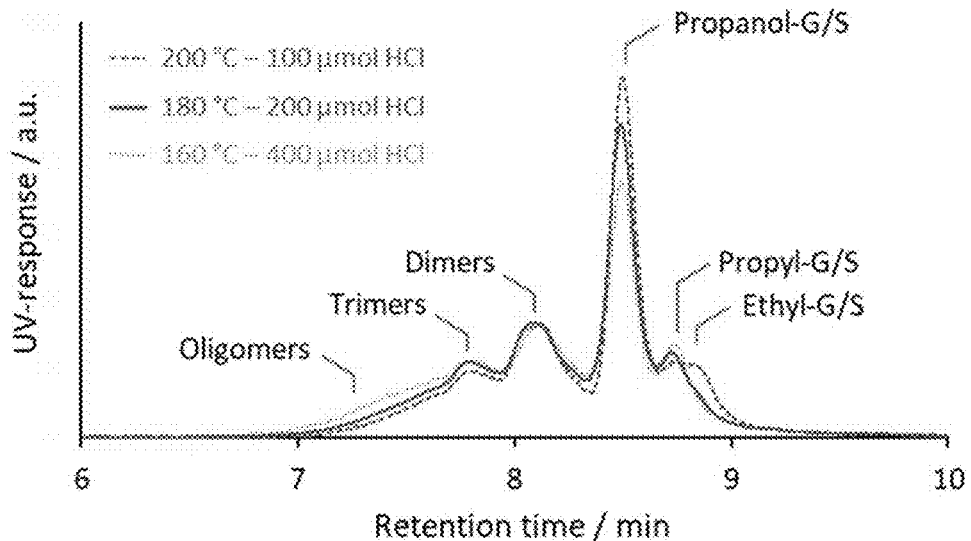
FIGS. 9A and 9B show GPC of lignin product oil (n-butanol phase) obtained with different temperature-[HC1] combinations (FIG. 9A). Additional chromatograms are shown in FIG. 9B) C5 polyol yield in function of C5 solubilisation (i.e. xylan and arabinan). Reaction conditions: 2 g Eucalyptus, 0.2 g Ru/C, 20 mL water, 20 mL n-butanol, 2 h, 30 bar $H_2$.
Figure 9B:
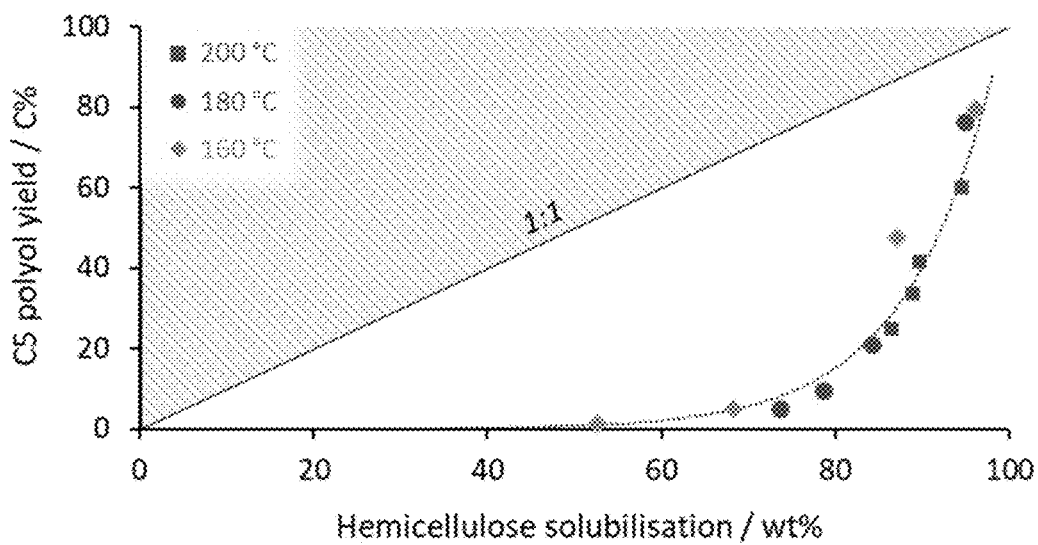

Results are summarised in FIG. 8B depicts the yield of carbohydrate monomer products in the aqueous phase, in function of temperature and acidity. At all three temperatures, the yield of targeted C5 polyols increases with increasing acidity. The highest yield of C5 polyols equals 150 mg $g_{biomass}^{-1}$ (80 C %), and was obtained at 160° C. with 400 µmol HCl. This yield is similar to the C5 polyol yield obtained in pure water at 200° C. (143 mg $g_{biomass}^{-1}$, FIG. 8B). Note that each temperature-acidity combination results in a unique process severity and therefore a different hemicellulose conversion. A comparison is therefore not straightforward. To overcome this issue, the C5 polyol yield was plotted in function of C5 solubilisation (FIG. 9B), which is a measure for hemicellulose conversion. FIG. 9B shows an exponential increase of the C5 polyol yield in function of C5 solubilisation. The deviation from the theoretical 1:1 conversion-yield relationship indicates that oligomers predominate under low severity conditions. Oligomer hydrolysis thus occurs more slowly and requires more severe conditions than hemicellulose solubilisation. Furthermore, the data points in FIG. 8B form one exponential curve, independent of temperature. This suggests that hydrolytic hydrogenation of hemicellulose during RCF is rather a function of process severity in general, in contrast to lignin conversion, which is favoured at high temperature—low acidity (vide supra, FIG. 8A), at least under the studied conditions. Overall, these experiments show that small amounts of acidic additive (in this example HCl) can assist the envisioned catalytic biorefinery process, though, balancing the different parameters that determine process severity is key (i.e. temperature, acidity, reaction time).

Example 10

Figure 10:
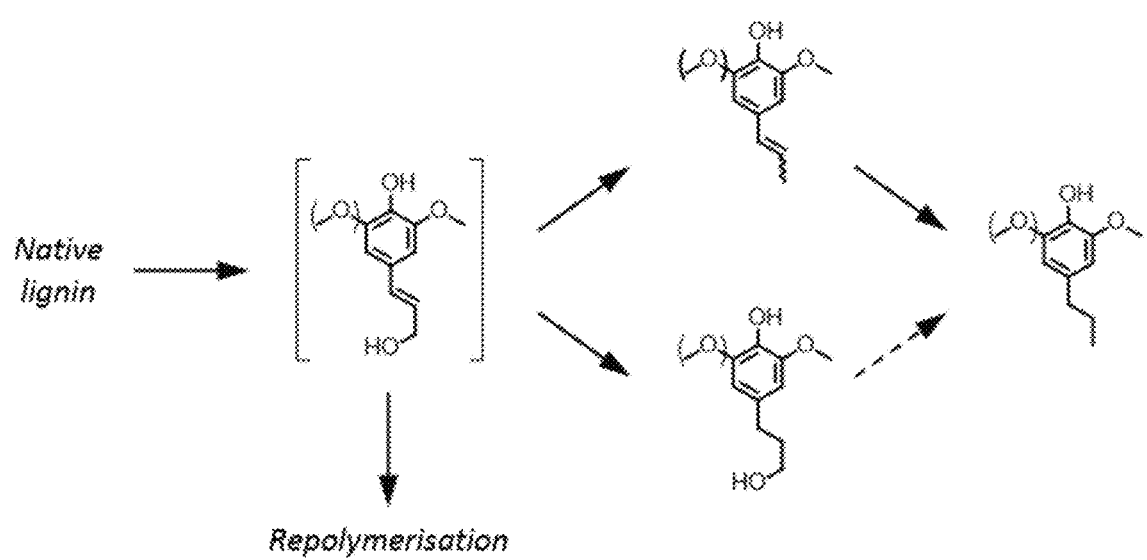
FIG. 10 is Scheme 1, which shows the proposed reaction network of lignin depolymerisation to phenolic monomers. Under the studied reaction conditions, formation of propyl-substituted monomers occurs primarily through the upper pathway (hydrogenolysis-hydrogenation), which predominates under low hydrogen pressure. Direct hydrogenation yielding propanol-substituted compounds is favoured under high hydrogen pressure (FIG. 6A).
Figure 11A:
FIGS. 11A-11C show a summary varying the reaction time.
Figure 11A:
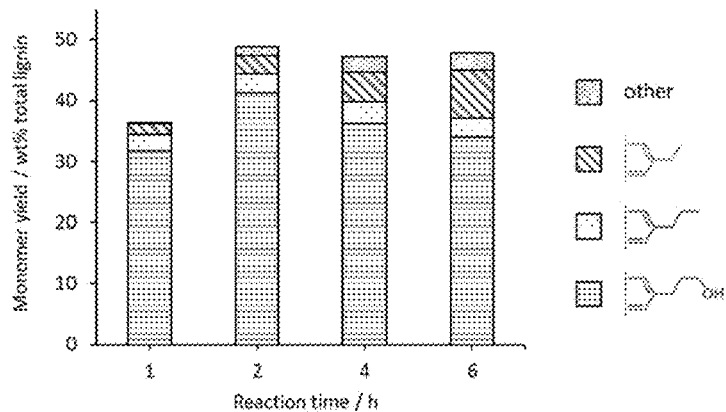

The effect of changing the reaction time is shown. The process as described in EXAMPLE 1 was performed for different reaction times, in the range of 1 h-6 h. Results are shown in FIG. 11A shows the total monomer yield and phenolic product selectivity. A maximum yield of propanol-G/S is reached for a 2 h reaction time. For shorter reaction times, the yield is lower because not all lignin is extracted yet. For longer reaction times, the selectivity to propanol-G/S slightly decreases because of secondary reactions (i.e. conversion to ethyl-G/S). However, the yield of propanol-G/S remains above 30 wt % for the investigated time range. The yield of propyl-substituted-G/S remains constant, indicating that propanol-G/S is not converted into propyl-G/S in the process of the current invention (FIG. 10, hashed arrow).

Figure 11B:
Figure 11B:
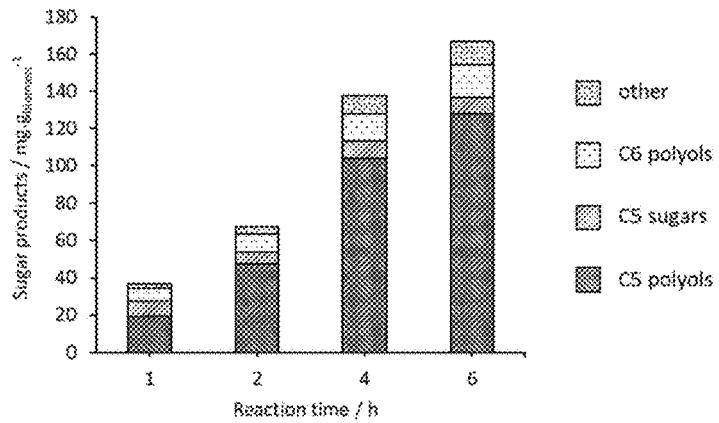
Figure 11C:
Figure 11C:
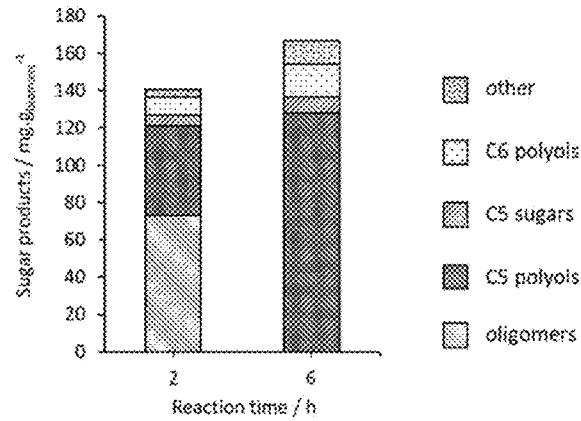

The yield of C5-polyols for different reaction times is displayed in FIG. 11B. The yield increases with reaction time, mainly because hemicellulose-derived oligomers are hydrolysed to monomeric sugar-derivatives. This is displayed in FIG. 11 C: the sum of C5-derived polyols and oligomers is approximately equal (in the range of 120-130 mg·g$^{-1}$ biomass) for a 2 h and 6 h reaction time.

Example 11

Figure 14:
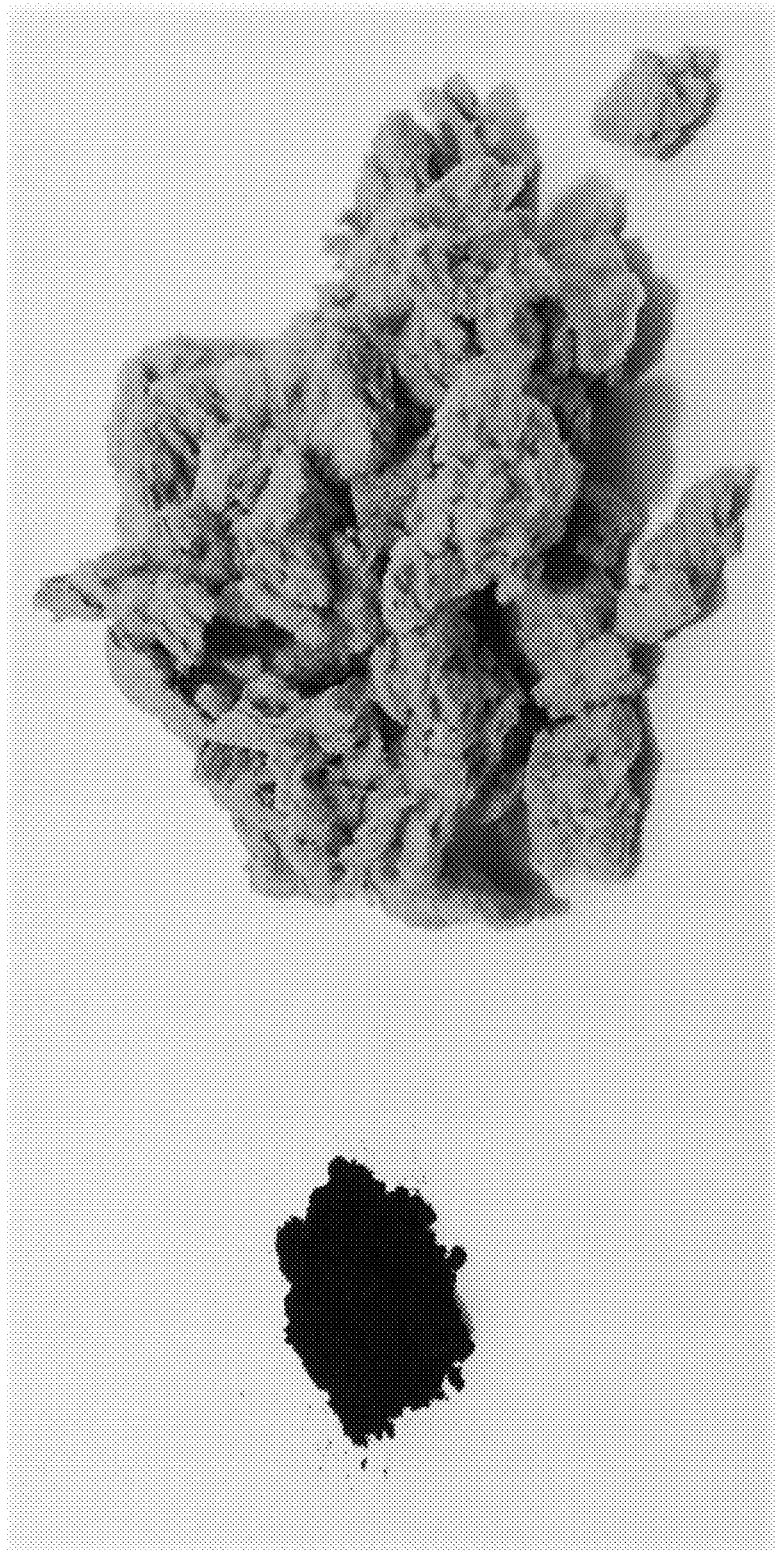
FIG. 14 is an image of isolated catalyst (left) and isolated pulp (right), obtained by washing the residual solids after reaction with n-butanol and water. The isolated black powder (circa 0.2 g) equals 98.1 wt% of the initial catalyst. The isolated pulp (circa 1 g) equals 96.4 wt% of the pulp mass.

This example demonstrates the recovery and reuse of the catalyst. The process of the invention was performed according to the steps described in EXAMPLE 1. The obtained solid residue, comprising pulp and spent Ru/C catalyst, was submersed in a fresh 2:1 (v:v) mixture of n-butanol and water. The mixture was stirred for 2 h using a magnetic stirring bar. Next, stirring was stopped and the butanol phase was collected. The carbon-supported catalyst is relatively apolar and primarily resides in the n-butanol phase. The pulp on the other hand is located at the bottom of the aqueous phase. Next, fresh n-butanol was added. This was repeated 5 times. Next, the aqueous and organic phase were filtered. The isolated black powder (circa 0.2 g) equals 98.1 wt % of the initial catalyst. The isolated pulp (circa 1 g) equals 96.4 wt % of the pulp mass. Images are displayed in FIG. 14.

Figure 15A:
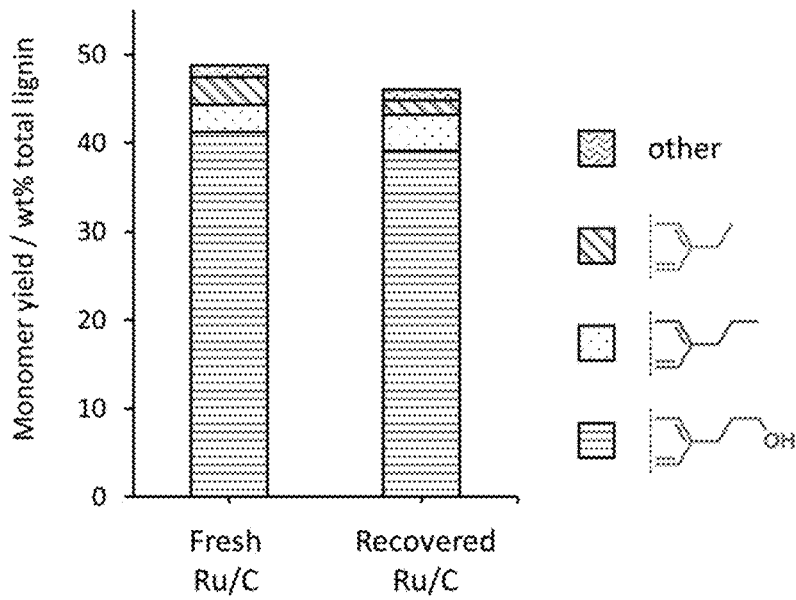
FIGS. 15A and 15B are a comparison of phenolic monomer yields (FIG. 15A) and sugar-derived monomers (FIG. 15B), obtained with a fresh and reused Ru/C catalyst. Reaction conditions: 20 mL water, 20 mL butanol, 0.2 g catalyst, 2 g Eucalyptus sawdust, 200° C., 2 h, 30 bar H$_2$.
Figure 15B:
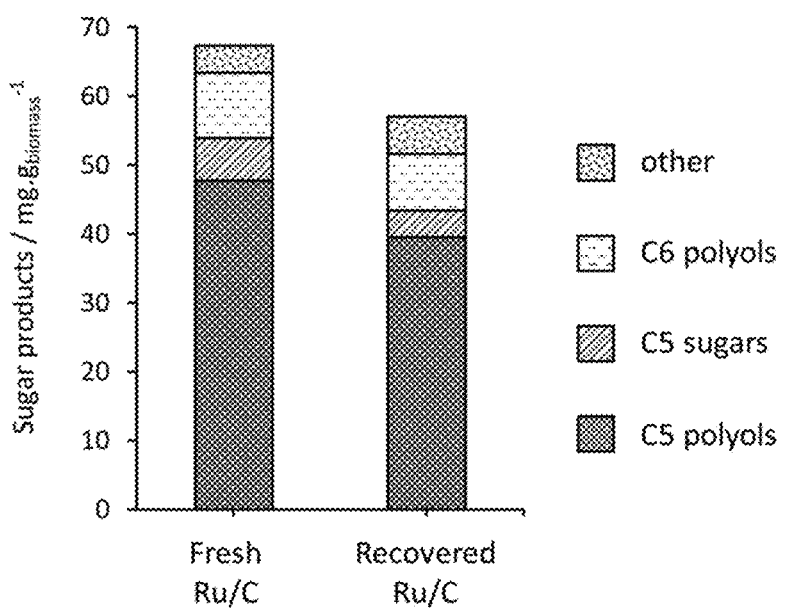

The recovered catalyst was used to verify reusability, according to the steps described in EXAMPLE 1. The recycled catalyst provided a quasi-similar lignin monomer yield (46.0 wt %) compared to fresh Ru/C (48.8 wt %), with high selectivity towards propanol-substituted monomers (FIG. 15). The obtained C5 polyol yield is slightly lower (40 vs. 48 mg g-1 biomass), whereas the pulp yield is similar (48.8 vs. 50.4 wt %). To conclude, this recycle experiment confirms that the spent Ru/C can be reused and displays good catalytic activity.

Example 12

Figure 16A:
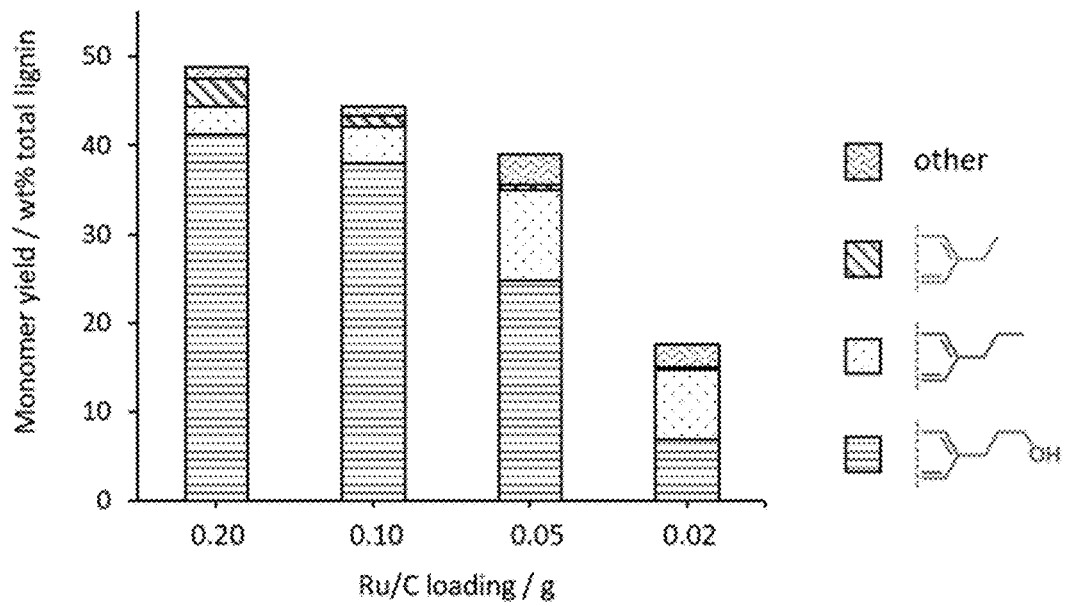
FIGS. 16A and 16B are a comparison of phenolic monomer yields (FIG. 16A) and sugar-derived monomers (FIG. 16B), obtained with different Ru/C amounts. Reaction conditions: 20 mL water, 20 mL butanol, 0.2 g Eucalyptus sawdust, 200° C., 2 h, 30 bar H$_2$.
Figure 16B:
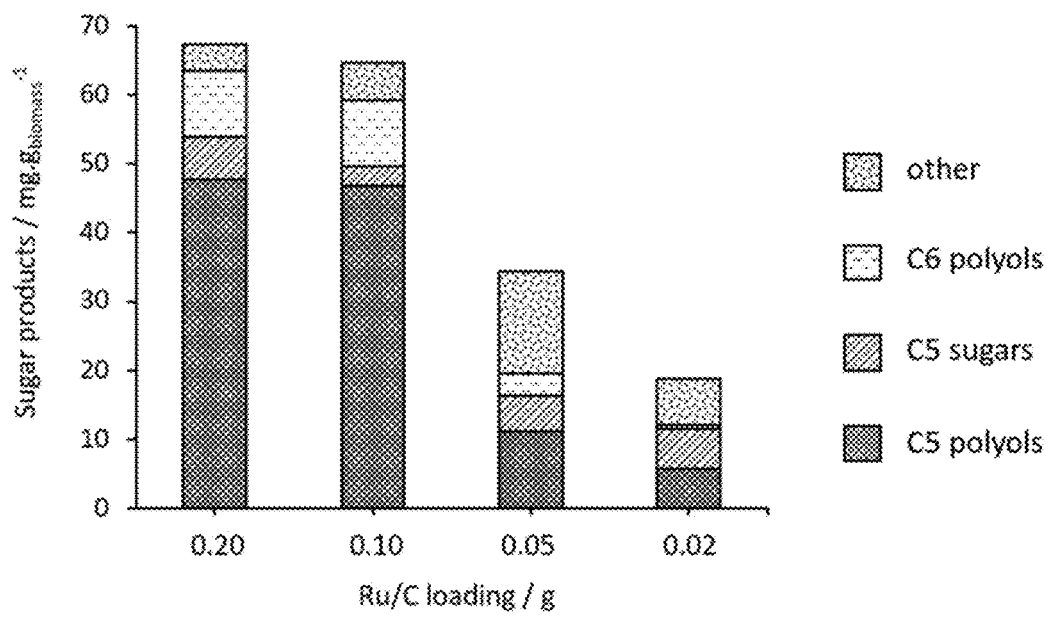

The effect of the catalyst-to-biomass ratio is shown (FIGS. 16A and 16B). The process as described in EXAMPLE 1 was performed with different amounts of catalyst (0.2 g, 0.1 g, 0.05 g and 0.025 g). Lowering the Ru/C (5 wt % metal) loading from 0.2 g (reference conditions, EXAMPLE 1) to 0.1 g has only a minor effect on both the lignin monomer yield and C5 polyol yield. Hence, the n-butanol/water RCF process works effectively with 5 wt % Ru/C relative to the biomass, which corresponds to 0.25 wt % metal. Further lowering the amount of Ru/C negatively impacts the conversion of lignocellulose. The lignin monomer yield decreases down to 39.1 wt % (0.05 g Ru/C) and 17.6 wt % (0.02 g Ru/C), indicating that lignin depolymerisation-stabilisation becomes less effective. Likewise, also the C5 polyol yield and selectivity drop when the loading of Ru/C equals 0.05 g or less.

It is noted that appropriate catalyst-to-biomass ratio depends on the catalyst type as on the feedstock type. For example, a more active catalyst can be added in lower amounts. A more dirty feedstock type (e.g. waste biomass, extractive rich biomass, mineral rich biomass) can lead to more extensive catalyst fouling/deactivation, requiring more catalyst to maintain an appropriate catalytic activity.

Example 13

Figure 17A:
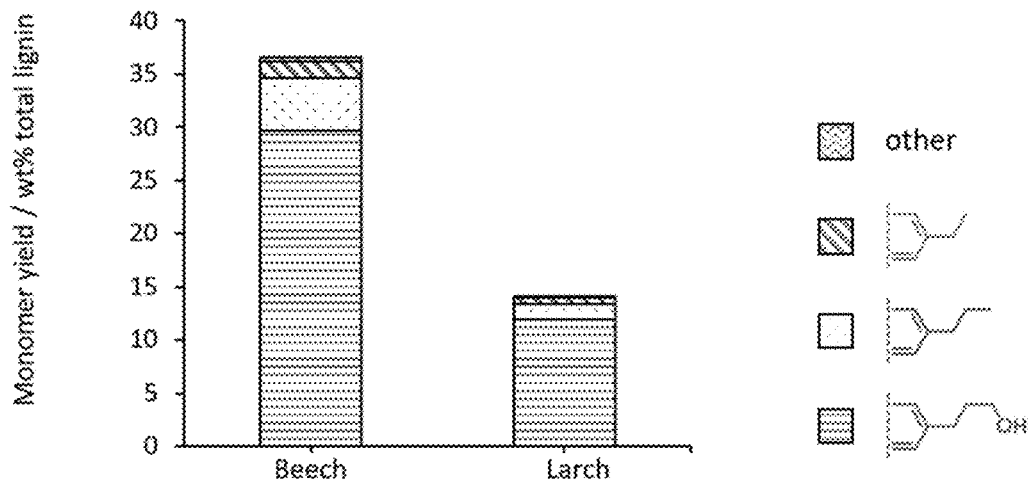
FIGS. 17A and 17B are a comparison of phenolic monomer yields (FIG. 17A) and sugar-derived monomers (FIG. 17B), obtained with different feedstocks (beech and larch), Reaction conditions: 20 mL water, 20 mL butanol, 0.2 g catalyst, 2 g Eucalyptus sawdust, 200° C., 2 h, 30 bar H$_2$.
Figure 17B:
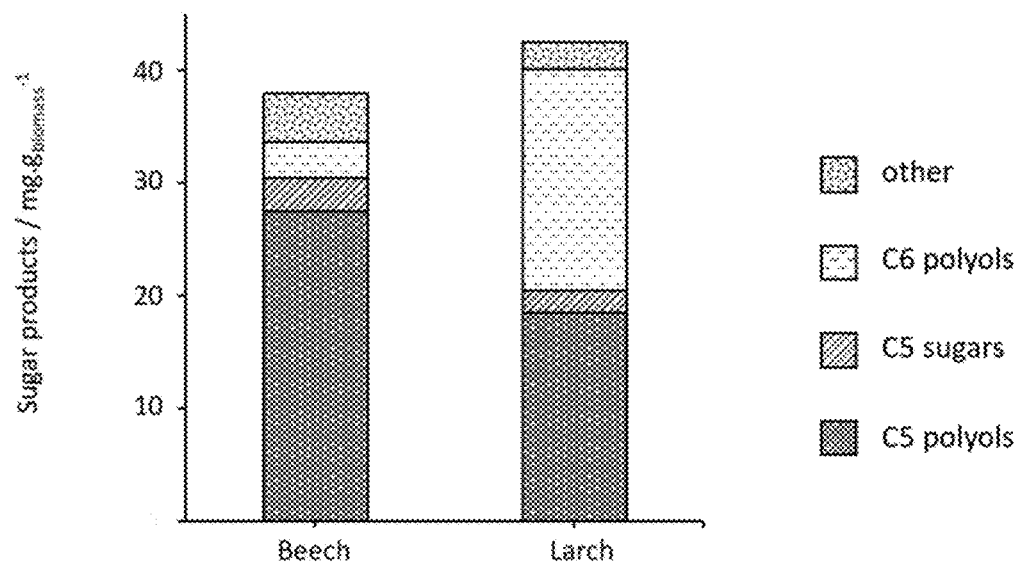

The applicability of other feedstocks is demonstrated. The process as described in EXAMPLE 1 was performed with beech wood (a hardwood species) and larch wood (a softwood species). Results are shown in FIGS. 17A and 17B. For beech wood, the total monomer yield equals 36.5 wt % relative to the initial lignin content. 81.5 wt % of the obtained monomers are propanol-substituted monomers. A C5 polyol yield of 27.5 mg per g biomass was obtained. For larch wood, the total monomer yield equals 14.2 wt % relative to the initial lignin content. 84.1 wt % of the obtained monomers are propanol-substituted monomers. A C5 polyol yield of 18.5 mg per g biomass was obtained. A C5 polyol yield of 19.5 mg per g biomass was obtained, which is much higher than the C6 polyol yield for beech (3 mg per g biomass). The differences between beech (hardwood) and larch (softwood)—see FIGS. 17A and 17B are due to the different biomass structure. For example, the lignin in larch has a lower content of cleavable inter-unit bonds (i.e. ether bonds) than the lignin in beech wood. Since these type of linkages are cleaved in the process according to the invention, the monomer yield for softwood is lower than for hardwood. Another difference: the hemicellulose in hardwood (beech, *Eucalyptus*) mainly comprises xylan (i.e. C5 units). Therefore, the obtained polyols are mainly C5 polyols. The hemicellulose for softwood comprises xylomannan (i.e. C5 and C6 sugars). Therefore, the obtained polyols are a mixture of C5 polyols and C6 polyols, with the amount of C6 polyols being higher for softwood than for hardwood species.

Example 14

The applicability of liquid media with different alcohol-to-water ratio's is demonstrated. The process as described in EXAMPLE 1 was performed with 30 mL BuOH and 10 mL water. The yield of propanol-substituted monomers equals 32.6 wt %, whereas the yield of propyl-substituted monomers equals 2.0 wt %, exemplifying that a high selectivity towards propanol-substituted monomers is obtained. In addition, the process as described in EXAMPLE 1 was performed with 10 mL BuOH and 30 mL water. The yield of propanol-substituted monomers equals 31.3 wt %, whereas the yield of propyl-substituted monomers equals 2.93 wt %. The total monomer yield for both experiments equals 36.8 wt % and 40.3, respectively. The yield of C5 polyols is 9.2 mg and 114.8 mg per gram biomass, respectively. This large variation is explained by the fact that a higher water content leads to a more polar reaction medium, which enhances the rate of hemicellulose hydrolysis, and thus higher C5 polyol yields. See also EXAMPLE 9 and EXAMPLE 10 on hemicellulose hydrolysis and the ratio of monomeric polyols to oligosaccharides.

Example 15

In addition to the utilisation of alcohol solvents that are not fully miscible at room temperature, such as n-butanol, the implementation of alcohol solvents that are miscible with water is shown. The process as described in EXAMPLE 1 was performed with 20 mL ethanol and 20 mL water instead of using a butanol/water mixture. The reaction was performed for 4 h, at a reaction temperature of 210° C. After the reaction, the reactor contents were filtered and washed with ethanol. The products in the liquid phase were isolated by evaporating the solvent mixture (ethanol and water), followed by threefold liquid-liquid extraction using 100 mL water and 3×33 mL n-butanol. A total phenolic monomer yield of 52.1 wt % was obtained, relative to the initial lignin content of the *Eucalyptus* wood. The yield of propanol-substituted monomers equals 37.7 wt %, whereas the yield of propyl-substituted monomers equals only 7.0 wt %, exemplifying the high yield and high selectivity towards propanol-substituted monomers (72.4 wt % selectivity). The C5 polyol equals 95.4 mg per gram biomass, 92 wt % of this comprises xylitol. The C6 polyol yield equals 16.7 mg per gram biomass.

Particular and preferred aspects of the invention are set out in the accompanying independent and dependent claims. Features from the dependent claims may be combined with features of the independent claims and with features of other dependent claims as appropriate and not merely as explicitly set out in the claims.

Thus, the claims following the detailed description are hereby expressly incorporated into this detailed description, with each claim standing on its own as a separate embodiment of this invention.

What is claimed is:

1. A process for producing polyols and phenolic compounds, the process comprising:
    combining lignocellulose, a lignocellulosic material, or a feedstock comprising lignocellulose, with (a) a liquid medium comprising water and an alcohol not fully miscible with water below 100° C., (b) an active catalyst consisting of ruthenium on carbon, and (c) hydrogen gas at a partial pressure of 10 bar or higher at room temperature to form a reaction mixture; and
    subjecting the reaction mixture to a temperature of at least 150° C. to form a product, wherein the product comprises:
        a mixture of sugar-derived polyols and oligosaccharides; and
        a mixture of phenolic compounds selected from monophenolic compounds, diphenolic compounds, and polyphenolic compounds, wherein the mixture of phenolic compounds comprises monophenolic compounds and at least 60% by mass of the monophenolic compounds have the general formula

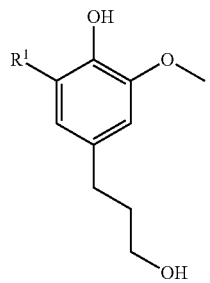

where $R^1$ is —H, —OH, or —OCH$_3$.

2. The process of claim 1, comprising:
(A) subjecting a feedstock medium to a temperature of at least 150° C., the feedstock medium comprising the lignocellulose, the lignocellulosic material, or the feedstock comprising lignocellulose in the liquid medium;
(B) subjecting a catalyst medium to a temperature of at least 150° C. under hydrogen atmosphere, the catalyst medium comprising the catalyst in water and alcohol; and
(C) supplying the feedstock medium to the catalyst medium.

3. The process of claim 1, wherein the product further comprises a cellulose-enriched solid material.

4. The process of claim 3, wherein the hydrogen gas is externally supplied and at a partial pressure of from 10 bar to 30 bar at room temperature.

5. The process of claim 1, wherein the liquid medium is a biphasic mixture when below 100° C.

6. The process of claim 5, wherein the alcohol in the liquid medium is selected from the group consisting of 1-butanol, 1-pentanol, 2-pentanol, 3-methylbutan-1-ol, 2-ethyl hexan-1-ol, and mixtures thereof.

7. The process of claim 5, further comprising separating the phenolic compounds from the sugar-derived polyols and oligosaccharides by performing liquid-liquid extraction using the liquid medium.

8. The process of claim 1, wherein the temperature is from 150° C. to 240° C.

9. The process of claim 1, wherein the mixture is subjected to the temperature for a reaction time of from 0.05 hours to 12 hours.

10. The process of claim 1, wherein the liquid medium has a ratio of alcohol to water of from 20:80 to 80:20 on a volumetric basis.

11. The process of claim 1, wherein the catalyst is spatially separated from the lignocellulose, lignocellulosic material, or feedstock comprising lignocellulose.

12. The process of claim 1, wherein the liquid medium further comprises a Lewis acid catalyst selected from the group consisting of AlCl$_3$, ZnCl$_2$, FeCl$_3$, Ni(II)-triflate, Cu(II)-triflate, Al(III)-triflate, Yb(III)-triflate, Sc(III)-triflate, La(III)-triflate, Hf(IV)-triflate, and combinations thereof.

13. A process for producing polyols and phenolic compounds, the process comprising:
    combining lignocellulose, a lignocellulosic material, or a feedstock comprising lignocellulose with (a) a liquid medium comprising water and an alcohol not fully miscible with water below 100° C., (b) an active catalyst consisting of ruthenium on carbon, and (c) hydrogen gas at a partial pressure of 10 bar or higher at room temperature to form a biphasic reaction mixture; and
    subjecting the biphasic reaction mixture to a temperature of at least 150° C. to form a product, wherein the product comprises:
        a mixture of sugar-derived polyols and oligosaccharides; and
        a mixture of phenolic compounds selected from monophenolic compounds, diphenolic compounds, and polyphenolic compounds, wherein the mixture of phenolic compounds comprises monophenolic compounds and at least 60% by mass of the monophenolic compounds have the general formula

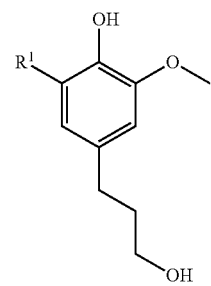

where $R^1$ is —H, —OH, or —OCH$_3$.

* * * * *